(12) United States Patent
Winkler et al.

(10) Patent No.: US 11,648,103 B2
(45) Date of Patent: May 16, 2023

(54) ARTIFICIAL VASCULAR GRAFT

(71) Applicant: UNIVERSITÄTSSPITAL BASEL, Basel (CH)

(72) Inventors: Bernhard Winkler, Bern (CH); Martin Grapow, Basel (CH); Friedrich Eckstein, Basel (CH); Aldo Ferrari, Zurich (CH); Dimos Poulikakos, Zollikon (CH); Simone Bottan, Zurich (CH); Maximilian Fischer, Munich (DE); Tobias Lendenmann, Zurich (CH)

(73) Assignee: UNIVERSITÄTSSPITAL BASEL, Basel (CH)

( * ) Notice: Subject to any disclaimer, the term of this patent is extended or adjusted under 35 U.S.C. 154(b) by 518 days.

(21) Appl. No.: 16/215,690

(22) Filed: Dec. 11, 2018

(65) Prior Publication Data

US 2019/0159880 A1 May 30, 2019

Related U.S. Application Data

(62) Division of application No. 15/022,212, filed as application No. PCT/EP2014/069946 on Sep. 18, 2014, now Pat. No. 10,188,499.

(30) Foreign Application Priority Data

Sep. 19, 2013 (EP) ..................... 13185086

(51) Int. Cl.
*A61F 2/07* (2013.01)
*A61F 2/06* (2013.01)
(Continued)

(52) U.S. Cl.
CPC .................. *A61F 2/07* (2013.01); *A61F 2/06* (2013.01); *A61F 2/062* (2013.01); *A61F 2/90* (2013.01);
(Continued)

(58) Field of Classification Search
None
See application file for complete search history.

(56) References Cited

U.S. PATENT DOCUMENTS

| 2002/0161449 A1* | 10/2002 | Muschler ............ A61L 27/3608 623/23.51 |
| 2003/0009213 A1 | 1/2003 | Yang |

(Continued)

FOREIGN PATENT DOCUMENTS

| WO | 2007140320 | 12/2007 |
| WO | 2011133019 | 10/2011 |

OTHER PUBLICATIONS

Tyler et al., "Present status of reversed vein bypass grafting: Five-year results of a modern series", pp. 193-205; 1990.
(Continued)

*Primary Examiner* — Rebecca S Preston
(74) *Attorney, Agent, or Firm* — JMB Davis Ben-David

(57) ABSTRACT

The invention relates to an artificial vascular graft comprising a primary scaffold structure encompassing an inner space of the artificial vascular graft, said primary scaffold structure having an inner surface facing towards said inner space and an outer surface facing away from said inner space, a coating on said inner surface, wherein a plurality of grooves is comprised in said coating of said inner surface. The primary scaffold structure comprises further a coating on said outer surface. The primary scaffold structure and the coating on said inner surface and on said outer surface are d designed in such a way that cells, in particular progenitor cells, can migrate from the periphery of said artificial vascular graft through said outer surface of said coating, said primary scaffold structure and said inner surface to said inner space, if the artificial vascular graft is used as intended. The invention relates further to a method for providing said graft.

17 Claims, 7 Drawing Sheets

Figure 1:
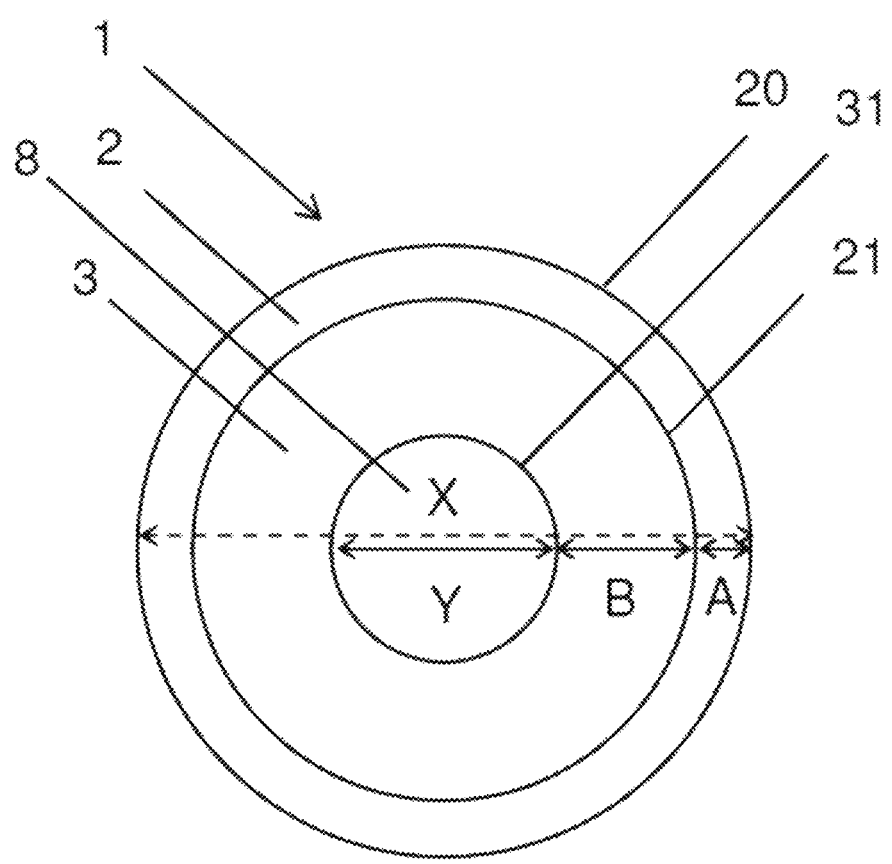

(51) Int. Cl.
  *A61F 2/90* (2013.01)
  *A61F 2/00* (2006.01)
  *C12N 1/20* (2006.01)

(52) U.S. Cl.
  CPC . *A61F 2002/0086* (2013.01); *A61F 2002/068* (2013.01); *A61F 2002/072* (2013.01); *A61F 2210/0014* (2013.01); *A61F 2210/0076* (2013.01); *A61F 2250/003* (2013.01); *A61F 2250/0026* (2013.01); *A61F 2250/0051* (2013.01); *A61F 2310/00011* (2013.01); *A61F 2310/00982* (2013.01); *C12N 1/20* (2013.01)

(56) References Cited

U.S. PATENT DOCUMENTS

| | | | | |
|---|---|---|---|---|
| 2003/0018454 | A1* | 1/2003 | Winkler | G06F 30/15 |
| | | | | 703/1 |
| 2006/0085063 | A1* | 4/2006 | Shastri | A61L 27/34 |
| | | | | 623/1.41 |
| 2008/0306580 | A1* | 12/2008 | Jenson | A61M 1/3655 |
| | | | | 623/1.11 |

OTHER PUBLICATIONS

Cameron et al., "Coronary Bypass Surgery With Internal-Thoracic-Artery Grafts—Effects on Survival Over a 15-Year Period", pp. 216-219; 1996.

Raja et al., "Saphenous Vein Grafts: To Use or Not to Use?", pp. 403-409: 2004.

Teebken et al., "Tissue Engineering of Small Diameter Vascular Grafts", pp. 475-485 ; 2002.

Mertens et al. "Surgical management of infainguinai arterial prosthetic graft infections: Review of a thirty-five-year experience", pp. 782-791; 1995.

Chen et al., "Adventitial Stem Cells in Vein Grafts Display Multilineage Potential That Contributes to Neointimal Formation", pp. 1844-1851; 2013.

Hu et al., "Differentiation and Function", 1523-1529; 2013.

Xiao et al., "Sca-1+ Progenitors Derived From Embryonic Stem Cells Differentiate Into Endothelial Cells Capable of Vascular Repair After Arterial Injury", pp. 2244-2251; 2006.

Santin M., "Tissue Engineering of Small- and Large- Diameter Blood Vessels", pp. 231-260; 2009.

\* cited by examiner

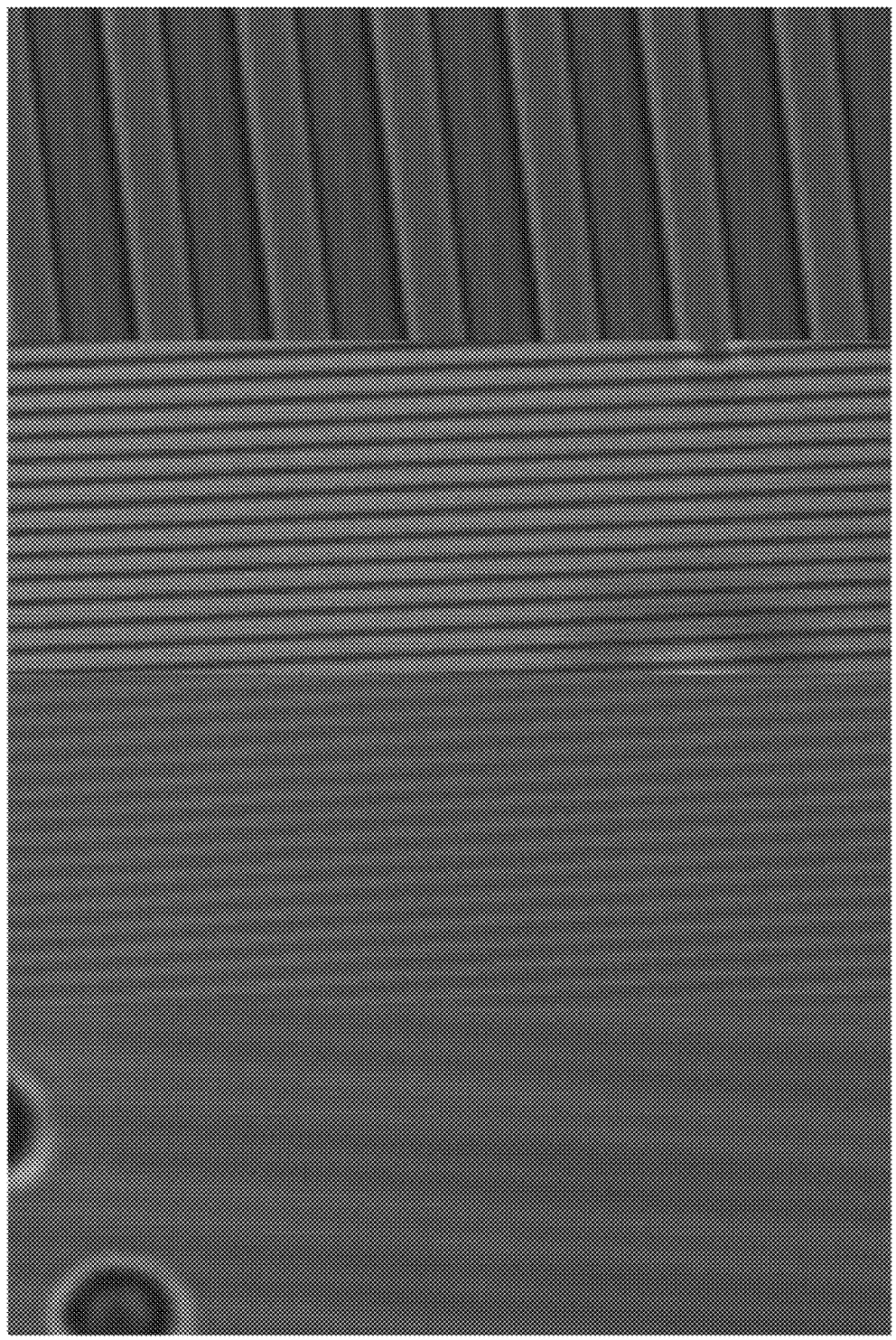

ARTIFICIAL VASCULAR GRAFT

FIELD OF THE INVENTION

The present invention relates to an artificial vascular graft having a structured surface. The invention further relates to a method for providing such a graft.

BACKGROUND OF THE INVENTION

The prevalence of arterial disease is increasing in many countries due to the ageing of society. This trend is of particular importance for atherosclerotic vascular diseases such as coronary and peripheral vascular diseases, which are leading causes of death in the western world. In general, their treatment and therapy involves a bypass by using the autologous saphenous vein for treatment of the lower limp artery (Tyler et al.; J. Vasc. Surg.; 11:193-205; 1990) or the internal mammary artery for a coronary artery bypass (Cameron et al.; N. Eng. J. Med.; 334:216-219; 1996). One major drawback of venous grafts, however, is occlusion (stenosis), which is a consequence of systemic pressure-induced tissue degeneration, whereby one-third of vein grafts are occluded within 10 years. Furthermore, half of those show marked atherosclerotic changes (Raja et al.; Heart Lung Circ.; 13:403-409; 2004).

An increasing amount of people (up to 30% according to WHO report on cardiovascular diseases 2010) who require cardiac surgery, a vascular surgical bypass or even a dialysis shunt, cannot be provided with suitable autologous bypass material, due to pre-existing diseases or because the bypass material has already been used in previous surgery. Thus, the demand on an artificial vascular replacement material, which comprises analogous characteristics as the native counterpart, is increasing.

Beside the urgent need for small diameter grafts (as for the coronary arteries or peripheral blood vessels), there is also a considerable lack of replacement materials concerning large diameter vessels (as for a diseased aorta or for the repair of congenital cardiovascular malformations).

Existing artificial vascular prostheses have serious limitations. One major problem concerning synthetic materials used as vascular substitutes is the patency rate of the grafts due to thrombogenicity and graft occlusion.

Particularly, the tissue engineered small-diameter vascular grafts comprise several severe shortcomings (Teebken and Haverich; Graft; 5; 14; 2002), despite the development of many strategies to fabricate vascular substitutes with anti-thrombogenic properties.

Early approaches focused on surface coating of synthetic grafts by seeding endothelial cells directly onto the vascular prosthesis prior to implantation. However, these synthetic grafts still induce low-level foreign body reaction and chronic inflammation and are associated with an increased risk of microbial infections (Mertens et al.; J. Vasc. Surg.; 21:782-791; 1995).

More recent strategies focused on the creation of complete autologous, living vascular substitutes using a three-dimensional temporary vehicle seeded with autologous cells (smooth muscle cells and endothelial cells in order to line the inner lumen), which are harvested and cultivated. After proliferation in sufficient numbers, the cells are seeded onto the three-dimensional scaffolds (based on synthetic or natural material) and exposed to a physiological in vitro environment in a bioreactor system. After several weeks the tissue formation and maturation is completed and the vascular substitutes are ready for implantation. Optionally a non-scaffold based vascular tissue engineering concept via cell sheets is used. One of the main disadvantages is the time consuming preparation, which renders these artificial grafts useless for patients in need of such an artificial graft on short notice, and restricts the application to non-urgent patients.

An overview of scaffold materials used in crating grafts has been published by Schmidt and Hoerstrup. (M. Santin (ed.); Strategies in Regenerative Medicine; Chapter 7; DOI 10.1007/978-0-387-74660-9_7).

Natural scaffolds employed include, inter alia, tanned bovine carotid arteries, polyethylene terephthalat (Dacron® DuPont) meshes embedded into the collagen or a collagen biomaterial derived from the submucosa of the small intestine and type 1 bovine collagen.

Furthermore, decelluarized tissues fabricated from either vascular or non-vascular sources were applied and implanted without any in vitro cell seeding, with the assumption that they will be recelluarized by host cells in vivo. However, significant shrinkage was observed in decelluarized vessels as a result of proteoglycans being removed from the tissues during the decelluarization process. Additionally, an adverse host response, aneurysm formation, infection and thrombosis after implanting decelluarized xenografts were observed.

As permanent synthetic scaffolds, polyurethane (PU) and loosely woven, relatively elastic, polyethylene terephthalat (Dacron® DuPont) based scaffolds were applied. However, the major limitation of these materials is lack of compliance. When used for repairing or replacing smaller diameter arteries, these grafts may fail due to occlusion by thrombosis or kinking, or due to an anastomotic or neointimal hyperplasia. Furthermore, expansion and contraction mismatches can occur between the host artery and the synthetic vascular prosthesis, which may result in anastomotic rupture, stimulated exuberant cell responses as well as graft failure due to disturbed flow patterns and increased stresses.

Concerning biodegradable synthetic scaffolds, several attempts were made to apply biodegradable polymers as temporary mechanical support for in vitro generated tissues. Particularly polyglycolic acid (PGA) or copolymers thereof, polylactid acid (PLA) and Poly-ε-caprolactone (PCL) were used as biodegradable polymers. The biodegradable synthetic material serves as a temporary scaffold and guides tissue growth and formation until the neo-tissue demonstrates sufficient mechanical properties, whereby—in theory—the scaffold will degrade completely after a certain time, providing a total autologous vascular graft. However, the difficult control of the ratio of degeneration, which has to be proportional to the tissue development, is one of the main drawbacks of these grafts. As a consequence, if the speed of material degradation is faster than regeneration of the tissue in the vascular graft, the graft may rupture.

There are many drawbacks considering the provision of artificial grafts. For example, matching the mechanical properties of large-diameter vessels for the replacement of the aorta—due to high pressure changes—is difficult. Such mechanical properties could only be obtained in long in vitro culture times, which render clinical application almost impossible. Furthermore, a long in-vitro culture time increases the risks of infection and cell dedifferentiation.

The demand for small diameter artificial grafts is very high. Especially with respect to the tissue engineering of small-diameter blood vessels, however, the mentioned problems could not be solved satisfactorily. These artificial grafts remain a particular challenge due to the lower flow velocity compared to large-diameter vessels. Bearing in mind the law of Hagen-Poiseuille, the volume of the flow is highly dependent on the radius of the tube, considering the flow characteristics of voluminal laminar stationary flows of incompressible uniform viscous liquids through cylindrical tubes with constant circular cross-sections.

The special problem associated with small-diameter grafts appears to be related primarily to the development of a fibrinous pseudointima, with gradual thickening that leads to thrombotic occlusion of the graft. However, patency rates of artificial small-diameter grafts are unacceptable in comparison to autologous vein and arterial grafts (Teebken and Haverich; Graft; 5; 14; 2002).

Thrombosis due to the reaction with foreign bodies or lack of endothelial cells, intimal hyperplasia caused by inflammatory reaction and compliance mismatch of the native vessel and the prosthetic graft at the anastomosis site are unsolved problems of particular importance.

In summary, existing grafts—especially small diameter grafts—have severe drawbacks such as the amount of time to produce in vitro grafts (e.g. via seeding of endothelial cells), thrombosis or the lack of the necessary stability.

Therefore, the provision of artificial grafts, in particular small-diameter artificial grafts, is highly desirable, in order to provide means of an optimal therapeutic artificial vascular graft, which can be used for a cardiovascular bypass operation for patients lacking suitable autologous bypass material.

It is an object of the present invention to improve on the above mentioned state of the art, in particular to provide safe and efficacious artificial grafts, which could be used instantly after unpacking, without the limitations of the existing artificial grafts, as well as a method to produce said grafts. This objective is attained by the subject matter of the independent claims.

BRIEF SUMMARY OF THE INVENTION

The invention provides an artificial vascular graft featuring a primary scaffold structure encompassing an inner space of the artificial vascular graft. The primary scaffold structure has an inner surface facing towards the inner space and an outer surface facing away from the inner space. The artificial vascular graft further comprises a coating on the inner surface of the primary scaffold structure. The coating, situated on the inner surface of the primary scaffold structure, has an inner coating surface facing the inner space of the artificial vascular graft. Additionally, the artificial vascular graft comprises a plurality of grooves in the coating of the inner surface of the primary scaffold structure. These grooves are situated on the inner coating surface of said coating, whereby the inner coating surface of the coating faces towards the inner space of the artificial vascular graft.

The primary scaffold structure comprises further a coating on said outer surface. The primary scaffold structure and the coating on said inner surface and on said outer surface are designed in such a way that cells, in particular progenitor cells, can migrate from the periphery of said artificial vascular graft through said outer surface of said coating, said primary scaffold structure and said inner surface to said inner space, if the artificial vascular graft is used as intended.

The artificial vascular graft comprises at least two openings.

The artificial vascular graft of the invention is intended to replace diseased or dysfunctional vascular tissue in a patient. Thereby, the openings of the graft are connected with one or more blood vessels. Particularly, the artificial vascular graft is used as a substitution of a part of a natural blood vessel, therefore, after removal of a part of the natural blood vessel, the ending of a blood vessel remaining in the patient is connected with one opening of the artificial vascular graft, whereby an other ending of a blood vessel is connected with another opening of the artificial vascular graft. This allows a flow of blood from one opening of the artificial vascular graft through to the other opening.

In some embodiments, the artificial vascular graft comprises more than two openings. By way of non-limiting example, the artificial graft can take the form of a Y-shaped vessel (a junction or furcation). This Y-shaped graft is similarly intended to be connected to blood vessels for blood flow.

The inner surface of the coating, which comprises the plurality of grooves, will be in contact with blood flowing through the artificial vascular graft, when the artificial vascular graft is used as intended.

Generally, the primary scaffold structure offers the necessary stability and structural integrity and supports the coating. In one embodiment, the primary scaffold structure comprises a coating on the inner and the outer surface of the primary scaffold structure. Thus, the coating encompasses the primary scaffold structure.

The artificial vascular graft with the features according to the invention may be used, inter alia, as an implant, in particular for blood vessels or cardiac valves. It may be further used as a dialysis shunt or as a tube for blood in and out flow in a life support machine.

In some embodiments, the primary scaffold structure and/or the coating is characterized by a generally tubular shape. The tubular shape may be branched, comprising one additional tubular branch (yielding a form comparable to the letter "Y") or more tubular branches.

In some embodiments, the primary scaffold structure comprises a generally tubular shape having an outer diameter in the range of about 1.5 mm to 40 mm, in particular of about 1 mm, 1.5 mm, 2 mm, 3 mm, 4 mm, 5 mm, 7.5 mm, 10 mm, 12.5 mm to 15 mm.

In some embodiments, the primary scaffold structure comprises a generally tubular shape having an outer diameter in the range of about 3.5 mm to 40 mm. In some embodiments, the primary scaffold structure comprises a generally tubular shape having an outer diameter in the range of about 3.5 mm to 15 mm.

The outer diameter of the primary scaffold structure is the maximal distance of two points situated on the outer surface of the primary scaffold structure, measured through the center of the tubular primary scaffold structure and in the plane, which extends vertical to the longitudinal extension direction of the primary scaffold structure.

In some embodiments, the primary scaffold structure comprises a generally tubular shape with an outer diameter in the range of about 6 mm to 40 mm, in particular of about 6 mm, 7 mm, 8 mm, 9 mm, 10 mm, 11 mm, 12 mm, 13 mm, 14 mm to 15 mm for use as a large-size diameter artificial vascular graft. In a further embodiment, the primary scaffold structure comprises a generally tubular shape with an outer diameter in the range of about 1.5 mm, 2 mm, 3 mm, 4 mm, 5 mm or 6 mm for use as a small-size diameter vascular artificial graft.

In one embodiment, the primary scaffold structure comprises a generally tubular shape with an outer diameter in the range of about 1.5 mm and 4 mm for use as a small-size diameter artificial vascular graft. In one embodiment, the primary scaffold structure comprises a generally tubular shape with an outer diameter in the range of about 4 mm and 6 mm for use as a small-size diameter artificial vascular graft.

In one embodiment, the primary scaffold structure comprises a generally tubular shape with an outer diameter in the range of about 3.5 mm and 5 mm, in particular of about 4.5 mm for use as a small-size diameter artificial vascular graft.

In some embodiments, the thickness of the primary scaffold structure (i.e. the distance between the inner and outer surface of the primary scaffold structure) is between 0.05 mm and 1 mm, in particular between 0.1 mm and 0.3 mm. In another embodiment, the thickness about 0.2 mm. In other words, the term "thickness" in this context refers to the difference between the outer diameter and the inner diameter of the primary scaffold structure, whereby the inner diameter of the primary scaffold structure is the maximal distance of two points situated on the inner surface of the primary scaffold structure, measured through the center of the tubular primary scaffold structure and in the plane, which extends vertical to the longitudinal extension direction of the primary scaffold structure.

In some embodiments, the primary scaffold structure has a length, measured in the longitudinal extension direction of the primary scaffold structure, of at least 1 cm. In another embodiment, the primary scaffold structure has a length, measured in the longitudinal extension direction of the primary scaffold structure, between 8 cm to 40 cm, in particular between 15 cm to 20 cm.

In some embodiments, the primary scaffold structure exhibits a physiological compliance comparable to a native vessel in order to withstand hemodynamic pressure changes without failure. Thus, the primary scaffold structure comprises a material that is characterized by a compliance in the range of 400 to 1000%/2.93 kPa (22 mm Hg), in particular in the range of 600 to 800%/2.93 kPa (22 mm Hg).

Unless otherwise indicated, the term "compliance" refers to the ability of the primary scaffold structure and/or the coating to distend and increase its volume with increasing inner pressure, when the artificial vascular graft is used as intended. Furthermore, the term "compliance" refers to the ratio of the diameter change of the primary scaffold and/or the coating as the artificial vascular graft expands in the radial direction in response to a given change in the inner pressure, and the values for compliance referred to below result from dynamic, in vitro testing.

In one embodiment, the burst pressure of the primary scaffold structure and the coating is higher than 133.32 kPa (1000 mm Hg).

In some embodiments, the primary scaffold structure comprises a material with a high tensile strength, in order to provide mechanical support to the artificial vascular graft, whereby the material of the primary scaffold structure is able to recoil to an original state after a symmetrical, radial expansion perpendicular to the longitudinal axis of the artificial vascular graft, wherein said radial expansion is in the range of 5% to 40%, in particular of 15% to 20%, with respect to the original outer diameter of the primary scaffold structure or the original inner diameter (see definition below) of the coating. In the following, it will be referred to as a flexibility of 5% to 40%, in particular of 15% to 20%. The term "original state" refers to the diameter size of the outer diameter of the primary scaffold structure or the inner diameter of the coating before use, particularly before exposing the graft to pressure. Thus, the primary scaffold structure comprises a flexible, resilient material, which enables recoil in order to prevent aneurysm formation.

In summary, the primary scaffold structure comprises mechanical properties similar to those of its natural counterpart, and provides a response to physiological changes by means of adequate vasoconstriction and relaxation when used as intended. That is, it functions without undue bulging or aggravated mismatching phenomena leading to graft failure.

In some embodiments, the primary scaffold structure comprises a plurality of holes, which are suited for a migration of cells, compounds and gases. In particular $O_2$ and $CO_2$, vascular growth factors, all humoral agents, progenitor cells capable of differentiating towards endothelial lineages and macrophages are allowed to migrate through the primary scaffold structure. In other words, the primary scaffold structure comprises a "perforated" structure, whereby the holes provide an opening, which reaches from the outer surface to the inner surface, thus, through the primary scaffold structure. Any kind of symmetric forms (for example round, oval, rectangular, etc.) or asymmetric forms are possible, as long as they allow said migration through the holes, while maintaining the necessary stability and structural integrity of the scaffold structure. Furthermore, a wire structure—comparable to cellulose—may be applied providing an interconnected hollow space in the primary scaffold structure. Thus allowing said migration. In other words, said "perforated" structure may comprise holes in form of a straight or branched tunnel or in form of an interconnected hollow space allowing said migration. In some embodiments, the diameter of the holes ranges from about 20 µm to 500 µm, in particular from about 20 µm to 300 µm. In some embodiments, the diameter of the holes ranges from about 35 µm to 50 µm. Also larger and smaller diameters may be employed.

In some embodiments, the diameter of the holes ranges from about 10 µm to 500 µm, in particular from about 10 µm to 200 µm. In some embodiments, the diameter of the holes ranges from about 10 µm to 100 µm. Also larger and smaller diameters may be employed.

In some embodiments, the primary scaffold structure comprises a mesh structure, in order to support the coating material and to allow the above discussed migration of cells, compounds and gases. In one embodiment, the primary scaffold structure may take the form of a knitted, braided or woven mesh structure. The primary scaffold structure may be appropriately crimped to provide the required resiliency and compliance, so that the primary scaffold structure is capable of a resilient radial expansion in a manner mimicking the compliance properties of a blood vessel, as discussed above.

In some embodiments, the primary scaffold structure may take the form of a wire mesh. In one embodiment, the wire thickness can be between 20 µm to 500 µm, in particular between 50 µm to 300 µm. In another embodiment, the wire thickness can be between 100 µm to 200 µm. In a further embodiment, the wire thickness can be between 50 µm to 150 µm.

In some embodiments, the maximal distance between neighboring wires can range from about 20 µm to 500 µm, in particular from about 100 µm to 300 µm. In one embodiment, the maximal distance between neighboring wires can range from about 20 µm to 100 µm. In one embodiment, the maximal distance between neighboring wires can range from about 35 µm to 50 µm. Thus, the wire mesh structure provides "holes" in the surface with an area of about 400 µm$^2$-250 000 µm$^2$, depending on the selected maximal distances. The wire mesh may have the form of a crisscrossed pattern or may comprise interconnected loops. In some embodiments, the maximal distance between neighboring wires is identical.

In some embodiments, the maximal distance between neighboring wires can range from about 10 µm to 500 µm, in particular from about 10 µm to 200 µm. In one embodiment, the maximal distance between neighboring wires can range from about 10 µm to 100 µm. Thus, the wire mesh structure provides "holes" in the surface with an area of about 100 µm$^2$-250 000 µm$^2$, depending on the selected maximal distances. The wire mesh may have the form of a criss-crossed pattern or may comprise interconnected loops. In some embodiments, the maximal distance between neighboring wires is identical.

In some embodiments, the primary scaffold structure and/or the coating comprise or consist of a biostable material. The term "biostable" material, used in context of this invention, is to be understood as a material with the ability to essentially maintain its physical and chemical integrity after implantation in living tissue. It has to be understood that a slight degradation (respectively a slow decomposition) of the applied material over a long period of time is considered as "biostable" in the context of the present specification.

In some embodiments, the primary scaffold structure and/or the coating comprise or consist of a degradable material. The term "degradable" material, used in context of the present specification, is to be understood as a material that will be broken down (degraded)—after implantation in living tissue during the course of time, in particular 50% of the original material will be degraded within between 3 to 24 months after implantation.

Thus, "biostable" material is to be considered as physically and chemically inert over a long period of time, whereby "degradable" materials will degrade over time.

In one embodiment, the primary scaffold structure comprises or consists of a corrosion resistant, biostable metal, in particular unalloyed commercial pure titanium (cp-Ti). The cp-Ti may be employed in different commercial available grades, in particular grades 1 to 4 (according to ASTM (American Society for Testing and Materials) F67-06: Grade 1-UNS (Unified Numbering System) R50250; Grade 2-UNS R50400; Grade 3-UNS R50550; and Grade 4-UNS R50700).

In another embodiment, the primary scaffold structure comprises or consists of a corrosion resistant, biostable metal alloy, in particular a high grade steel, a Cobalt based alloy, a Nickel based alloy or a Titanium based alloy. In some embodiments, the primary scaffold structure comprises a CoCrMo- or CrNiMo-alloy.

In some embodiments, the primary scaffold structure comprises or consists of a biostable, corrosion resistant shape memory alloy. The shape memory alloy comprises so-called "superelastic" properties. Thus, the shape memory alloy can undergo large deformations under stress and then instantly revert back to the original shape when the stress is removed. The shape memory alloy comprises a flexibility of 5% to 40%, in particular of 15% to 20%. Furthermore, the shape memory alloy comprises a high durability, namely a very good strain-controlled fatigue performance. Thus, fatigue failures due to expansion and recoil of the shape memory alloy on basis of changing pressure inside the artificial graft, if it is used as intended, could not be observed over a prolonged period of time.

In some embodiments, the shape memory alloy comprises or consists of a titanium-palladium-nickel, nickel-zirconium-titanium, nickel-iron-zinc-aluminum and iron-manganese-silicon alloy.

In another embodiment, the primary scaffold structure comprises or consists of a shape memory alloy with 50 to 60% nickel (Reference) and 40 to 50% titanium (Balance), in particular 54.5% to 57.0% nickel (Reference) and 43.0 to 45.5% titanium (Balance) according to the Standard Specification for Wrought Nickel-Titanium Shape Memory Alloys for Medical Devices and Surgical Implants (ASTM F2063-05; Nitinol).

In a further embodiment, the nickel-titanium alloy (Nitinol) comprises a flexibility of 5% to 40%, in particular of 15% to 20%. Thus, the primary scaffold structure is able to recoil after a symmetrical radial expansion of 5% to 40%, in particular of 15% to 20%, with respect to the original diameter of the primary scaffold structure. Furthermore, the primary scaffold structure material comprises compliance in the range of 600 to 800%/2.93 kPa (22 mm Hg).

In some embodiments, the primary scaffold structure and/or the coating comprise or consist of a polymer material.

In some embodiments, the polymer material comprises or consists of a synthetic, blostable polymer like polyethylene terephthalate (PET), polypropylene (PP), polytetra-fluoroethylene (PTFE)), expanded polytetra-fluoroethylene (ePTFE), polyacrynitril (PAN) and polyurethane (PU).

In some embodiments, the polymer material comprises or consists of a biopolymer like a polypeptide or a polysaccharide, whereby the term "biopolymer" has to be understood as a polymeric material formed by living organisms. In some embodiments, the biopolymer comprises or consists of a biostable material like biostable collagen, in particular Collagen IV, or biostable cellulose.

In some embodiments, the polymer material comprises or consists of a shape memory polymer material, in particular polyurethane (PU), polyethylene terephthalate (PET), polyethyleneoxides (PEO), polystyrene, polytetrahydrofurane or polynorborene, whereby the shape memory polymer material comprises comparable characteristics as already discussed with respect to the shape memory alloys.

In some embodiments, the primary scaffold structure comprises a shape memory polymer material, which is reinforced by a shape memory metal alloy, in particular Nitinol.

In one embodiment, the primary scaffold structure comprises or consists of an elastomeric synthetic polymer or biopolymer material, e.g. a polyurethane elastomer or composite fibers that act in an elastic fashion. Further—not limiting—examples are fluoroelastomers (FKM), perfluoroelastomers (FFKM) or tetrafluoro ethylene/propylene rubbers (FEPM) and elastomeric polypeptides.

In some embodiments, the primary scaffold material and/or the coating comprise or consist of a degradable synthetic polymer or a degradable biopolymer material, in particular, polyglycolic acid (PGA) or copolymers thereof, polylactid acid (PLA), Poly-ε-caprolactone (PCL) or dextran.

In some embodiments, the primary scaffold structure and/or coating comprise or consist of a degradable biopolymer material, for example a cellulose material, such as cellulose ester, cellulose acetate or nitrocellulose and their derivatives (celluloid). In some embodiments, the primary scaffold structure and/or coating comprise or consist of a degradable biopolymer material, for example a degradable collagen material.

The above mentioned materials can be used for a primary scaffold structure comprising a knitted, braided or woven mesh structure as well as a wire mesh structure. In particular, the primary scaffold structure may take the form of a wire mesh made of metal, metal alloy or shape memory alloy. The same applies for the above discussed structures comprising holes.

In one embodiment, the eSVS MESHs Nitinol-mesh can be used as a primary scaffold structure, which could be purchased from Kips Bay Medical, Inc. Minneapolis, Minn., USA.

In some embodiments, the primary scaffold structure and the coating comprise or consist of a semipermeable material, in particular a semipermeable polymer material, so that cells and gases, in particular $O_2$ and $COO_2$, vascular growth factors, all humoral agents, progenitor cells capable of differentiating towards endothelial lineages and macrophages, can migrate through the primary scaffold structure and the coating to the inner coating surface of the coating, whereby the primary scaffold structure and the coating remains impermeable for the remaining substances of blood. The primary scaffold structure and the coating on said inner surface and on said outer surface are designed in such a way that cells, in particular progenitor cells, can migrate from the periphery of said artificial vascular graft through said outer surface of said coating, said primary scaffold structure and said inner surface to said inner space, if the artificial vascular graft is used as intended. Reference is made to the detailed explanation above concerning the semipermeable ability.

The migratory capacity of cells through the primary scaffold structure and the coating on said inner surface and on said outer surface can be tested according to the specifics as detailed in the publication of Chen et. al. (see Chen Y, Wong M M, Campagnolo P. Simpson R, Winkler B, Margariti A, Hu Y, Xu Q. "Adventitial stem cells in vein grafts display multilineage potential that contributes to neointimal formation. *Arterioscler Thromb Vasc* Biol. 2013, August; 33(8):1844-51. doi: 10.1161/ATVBAHA.113.300902).

The term "semipermeable" according to the invention is to be understood that the primary scaffold structure and the coating on the inner and outer surface of the primary scaffold structure are designed in such a way that that cells and gases, in particular $O_2$ and $CO_2$, vascular growth factors, all humoral agents, progenitor cells, more particular progenitor cells capable of differentiating towards endothelial lineages and macrophages, can migrate through the primary scaffold structure and the coating to the inner space (lumen) of the artificial vascular graft. If the artificial vascular graft is used as intended, substances of blood, such as thrombozytes, erythrocytes, leukocytes, cannot migrate from the inner space of the artificial vascular graft (lumen) through the primary scaffold structure and the coating on the inner and outer surface of the primary scaffold structure since platelets, also called "thrombocytes", will attach themselves on the coating facing the lumen and interconnect with each other providing an "impermeable wall" for the remaining substances of blood. However, cells and gases, in particular progenitor cells, are still capable to migrate from outside of the vascular graft towards the inner space (lumen)—due to the design of the artificial vascular graft—and through said impermeable wall provided by said thrombocytes.

Progenitor cells, such as mesenchymal stem cells, can migrate through the layers of other cells especially through thrombocytes or adhaerent cells by deformation and interaction.

The migration of progenitor cells to the lumen is particularly achieved by providing suitable holes, pores or interconnected hollow spaces, as discussed above and below of this section, allowing for the migration of progenitor cells capable of differentiating towards endothelial lineages and macrophages, to the inner space of the graft (lumen).

Progenitor cells capable of differentiating towards endothelial lineages and macrophages, are in particular mesenchymal stem cells, local tissue residential progenitor cells, especially adventitial residents and fat tissue residents such as epicardial progenitors or vein neighboring adventitial progenitors.

Vascular growth factors may migrate into or through the primary scaffold structure and the coating on the inner and outer surface from the periphery of the vascular graft but mainly from the blood inside the artificial vascular graft and enhance the migration of the cells by chemotaxis (the movement of an organism in response to a chemical stimulus).

In general, the major part of the progenitor cells, which amounts to about 80%, originate from the periphery of the artificial vascular graft and migrate through the "holes" or hollow spaces in the primary scaffold structure material and the coating material and only a small part (20%) stems from the blood inside the artificial vascular graft (see Hu Y, Xu Q. Adventitial biology: differentiation and function. *Arterioscler Thromb Vasc* Biol. 2011 July; 31(7):1523-9. doi: 10.1161/ATVBAHA.110.221176). Thus, a larger amount of the necessary progenitor cells are provided in the lumen of the graft for differentiation processes (as discussed below).

In some embodiments, the primary scaffold structure and/or the coating, in particular the coating, comprise or consist of a material providing hydrogen-bonding facilitating the cell migration (see Xiao Q, Zeng L, Zhang Z, Margariti A, Ali Z A, Channon K M, Xu Q, Hu Y. Sca-1+ progenitors derived from embryonic stem cells differentiate into endothelial cells capable of vascular repair after arterial injury. *Arterioscler Thromb Vasc* Biol. 2006 October; 26(10):2244-51.

In some embodiments, the primary scaffold structure comprises or consists of a fibroblast sheet. In some embodiments, the primary scaffold structure comprises an arterial, respectively venous decelluarized homograft or xenograft.

In general, the primary scaffold structure and/or the coating may be manufactured from any biologically acceptable material that possesses the ability to be shaped into the necessary structure, in particular a generally tubular structure, which allows for the above mentioned migration and comprises the required compliance and flexibility, as described above.

The flexibility of the above mentioned materials can be controlled by altering compositions, by crimping or tempering procedures. Furthermore, in case of wire mesh structures, by variation of the wire diameters or the distances of neighboring wires etc., so that the primary scaffold structure fashioned from this material may mimic the compliance values and flexibility of a native blood vessel, in particular in the aspects of timing, expansion and recoil.

In one embodiment, the coating covers the primary scaffold structure completely. In other words, the primary scaffold structure is completely embedded in the coating material. This prevents, if the artificial vascular graft is used as intended, an attachment of fibroblast and inflammatory cells on the primary scaffold structure. Furthermore, the coating prohibits an interaction of the material of the primary scaffold structure, if the artificial vascular graft is used as intended, with the surroundings, in particular with blood. In case of a metal or metal alloy material as a primary scaffold structure, the coating prohibits the separation of metal ions and the interaction of said ions with the human body.

In one embodiment, the coating comprises a generally tubular shape with a length, measured in the longitudinal extension direction of the coating, which is 2 mm to 20 mm, in particular 4 mm to 10 mm, longer than the length of the respective primary scaffold structure. Thus, the coating comprises a projection over the primary scaffolds structure.

This projection provides protection, while connecting a blood vessel with the artificial vascular graft during anastomosis—if the artificial vascular graft is used as intended.

In one embodiment, the material of the coating is able to recoil after a symmetrical, radial expansion of 5% to 40%, in particular of 15% to 20%, with respect to the original diameter of the coating (also referred to as flexibility).

In another embodiment, the coating comprises a material which provides similar mechanical properties as their native counterpart (e.g. a blood vessel). Thus, the coating comprises a material characterized by a compliance in the range of 400 to 1000%/2.93 kPa (22 mm Hg), in particular in the range of 600 to 800%/2.93 kPa (22 mm Hg).

Thus, the coating material comprises an elastic material, which is able to recoil in order to prevent aneurysm formation, and/or exhibits a physiological compliance comparable to a native vessel in order to withstand hemodynamic pressure changes without failure, if the artificial vascular graft is used as intended.

In some embodiments, the coating has a generally tubular shape with an inner diameter in the range of about 1 mm to 35 mm, in particular in the range of about 1 mm, 1.5 mm, 2 mm, 3 mm, 4 mm, 5 mm, 7.5 mm, 10 mm, 12.5 mm to 15 mm. The inner diameter of the coating is the maximal distance of two points situated on the inner coating surface of the tubular coating, measured through the center of the tubular coating and in the plane, which extends vertical to the longitudinal extension direction of the tubular coating. In some embodiments, the coating has a generally tubular shape with an inner diameter in the range of about 6 mm to 10 mm for the use as a large-size diameter artificial vascular graft. In some embodiments, the coating has a generally tubular shape with an inner diameter in the range of about 1 mm to 6 mm, in particular of about 4 mm to 6 mm for use as a small-size diameter artificial vascular graft. In some embodiments, the coating has a generally tubular shape with an inner diameter in the range of about 1 mm to 4 mm, in particular in the range of about 1 mm to 3.5 mm for use as a small-size diameter artificial vascular graft. Thus, the diameter of the inner coating surface of the coating allows a flow rate of 50 to 200 ml/min, without affecting the pulsation index, which is a factor of lower than five after anastomose.

In some embodiments, the coating has a thickness (whereby thickness is the difference between the outer and inner diameter of the coating) in the range of 0.5 mm to 6 mm, in particular in the range of 2 mm to 4 mm. The outer diameter of the coating is the maximal distance of two points situated on the outer coating surface of the tubular coating, measured through the center of the tubular coating and in the plane, which extends vertical to the longitudinal extension direction of the coating. In some embodiments, the coating is symmetrically distributed with respect to the primary scaffold structure. In other words, the distance from the outer surface of the primary scaffold structure to the outer coating surface of the coating is essentially the same as the distance from the inner surface of the primary scaffold structure to the inner coating surface of the coating.

In another embodiment, the coating is asymmetrically distributed around the primary scaffold structure. Thus, the coating comprises an inner thickness, which is the difference between the inner diameter of the coating and the inner diameter of the primary scaffold structure, and an outer thickness, which is the difference between the outer diameter of the coating and the outer diameter of the primary scaffold structure, whereby the value of the inner thickness is different to the value of the outer thickness. In one embodiment, the outer thickness is larger than the inner thickness of the coating.

In some embodiments, the primary scaffold structure and/or the coating comprise a symmetrical tubular structure. Thus, the primary scaffold structure and/or the coating comprise—throughout the tubular artificial vascular graft—a tubular structure with an essentially identical outer diameter of the primary scaffold structure and/or an essentially identical inner diameter of the coating.

In one embodiment, the coating comprises an inert and sterile material. In another embodiment, the coating comprises an anti-thrombogenic material. In some embodiments, the anti-thrombogenic material can be cellulose, Collagen IV, matrigel, heparin coated polymers and IPS (Induced pluripotent stem) cell generated neointima. In some embodiments, the anti-thrombogenic material can comprise ECM components (extracellular matrix), whereby the ECM is composed of three major classes, namely structural proteins, like collagen and elastin, specialized proteins, like fibrillin, fibronectin and laminin, and proteoglycans.

In some embodiments, the coating comprises a sterile, anti-thrombogenic and inert material. Thus, the coating is compatible for every patient and there is no need for additional anticoagulation and the artificial vascular graft can be used instantly for an implantation. In some embodiments, the material of the coating is resistant to infection after implantation and is designed to avoid inflammation and hyperplasia.

In some embodiments, the coating comprises or consists of a polymer or a degradable polymer, whereby the polymer or degradable polymer is sterile, anti-thrombogenic and inert.

In some embodiments, the coating comprises or consists of a cellulose material, which is biological inert and sterile. In one embodiment, the coating comprises or consists of a cellulose material with anti-thrombogenic abilities.

In some embodiments, the coating comprises or consists of a cellulose material, which is biologically inert, sterile and anti-thrombogenic.

In some embodiments, the cellulose material of the coating is able to recoil after a symmetrical, radial expansion (also referred to as flexibility) of 5% to 40%, in particular of 15% to 20%, with respect to the original inner diameter of the coating.

In some embodiments, the cellulose material of the coating exhibits a physiological compliance comparable to a native vessel in order to withstand hemodynamic pressure changes without failure and, thus, providing compliance in the range of 400 to 1000%/2.93 kPa (22 mm Hg), in particular in the range of 600 to 800%/2.93 kPa (22 mm Hg).

In some embodiments, the cellulose material of the coating comprises a semipermeable ability. Thus, cells and gases, in particular $O_2$ and $CO_2$, vascular growth factors, all humoral agents, progenitor cells capable of differentiating towards endothelial lineages and macrophages, can migrate through the cellulose material towards the inner diameter of the coating, whereby the coating material remains impermeable for the remaining substances of blood. Thus, the cellulose material—comprising a three-dimensional structure pattern in form of interconnected fibers—allows for a migration of cells, compounds and gases. In particular $O_2$ and $CO_2$, vascular growth factors, all humoral agents, progenitor cells, more particularly progenitor cells capable of differentiating towards endothelial lineages and macrophages to migrate through the cellulose material via the interconnected hollow space between the fibers of the cellulose material.

In other words, the cellulose material comprises "holes" respectively "porous" structure, whereby the interconnected hollow space provide an (indirect) opening, which reaches from the outer surface to the inner surface, thus, allowing said migration. In some embodiments, the mean diameter of the hollow space ranges from about 20 µm to 500 µm, in particular from about 20 µm to 300 µm. In some embodiments, the diameter of the holes ranges from about 35 µm to 50 µm. Also larger and smaller diameters may be employed. In some embodiments, the mean diameter of the hollow space ranges from about 10 µm to 500 µm, in particular from about 10 µm to 200 µm. In some embodiments, the diameter of the hollow space ranges from about 10 µm to 100 µm.

Concerning a further discussion of the "semipermeable ability" references is made to the detailed description above.

In some embodiments, the cellulose material of the coating is sterile, inert and comprises semipermeable and anti-thrombogenic abilities, as well as the above mentioned flexibility and compliance.

In one embodiment, the cellulose is derived from the bacteria *Acetobacter*, in particular *Acetobacter xylinum* strain ATTC 23769 and is sterile, inert and comprises semipermeable and anti-thrombogenic abilities, as well as the above discussed flexibility and compliance.

The cellulose fibers derived from said bacteria have a high aspect ratio with a diameter of 100 nm. As a result, said cellulose has a very high surface area per unit mass. The fibrous structure consists of a three-dimensional non-woven network of nanofibrils, sharing the same chemical structure as plant cellulose, which is held together by inter- and intra-fibrilar hydrogen bonding resulting in a never-dry hydrogel state with high strength.

In one embodiment, the primary scaffold structure and the coating comprise a flexibility of 5% to 40%, in particular of 15% to 20%, with respect to the original outer diameter of the primary scaffold structure or the original inner diameter of the coating, and a compliance in the range of 400 to 1000%/2.93 kPa (22 mm Hg), in particular in the range of 600 to 800%/2.93 kPa (22 mm Hg). Thus, the coating material is compatible for every patient and there is no need for additional anticoagulation and the artificial vascular graft is able to recoil in order to prevent aneurysm formation and exhibits a physiological compliance comparable to a native vessel in order to withstand hemodynamic pressure changes without failure, if the artificial vascular graft is used as intended. Particularly preferred is a flexibility of 15% to 20%. A too low flexibility will end in stiffness preventing the necessary arterial like pulsation and a too high flexibility will end in a high material swing ending in turbulent flow leading to restenosis.

In one embodiment, the coating comprises a polymer material, in particular a cellulose material, comprising the previously described features and the primary scaffold structure comprises a shape memory alloy, in particular Nitinol.

In one embodiment, the coating consists of a cellulose material comprising the previously described features and the primary scaffold structure comprises a shape memory alloy, in particular Nitinol. The primary scaffold structure and the coating comprise a flexibility of 5% to 40%, in particular of 15% to 20%, with respect to the original outer diameter of the primary scaffold structure or the original inner diameter of the coating, and a compliance in the range of 400 to 1000%/2.93 kPa (22 mm Hg), in particular in the range of 600 to 800%/2.93 kPa (22 mm Hg).

In some embodiments, the primary scaffold structure comprises holes or a mesh structure and is embedded in the coating material, in particular a cellulose material, in such a way, that the coating material reaches through the "holes" of the primary scaffold structure yielding to a strong connection between the primary scaffold structure and the coating.

Nevertheless, this has no impact on the semipermeable ability as discussed above.

In some embodiments, the coating comprises the same coating material on the outer surface and the inner surface of the primary scaffold structure, which is selected from the above mentioned materials. In some embodiments, the coating comprises different materials on the outer coating surface and on the inner coating surface, whereby each material is selected from the coating materials discussed above. In one embodiment, the outer surface comprises a coating of decelluarized fibroblasts or gelatin, whereby the inner surface comprises a coating material selected from the above mentioned materials.

In some embodiments, the primary scaffold structure and the coating are capable of providing a necessary stability after a cutting of the artificial vascular graft (the generally tubular shape will remain intact and particularly no parts of the primary scaffold structure, such as wire parts of the mesh, will be in contact with living tissue, due to the coating in which the primary scaffold structure is embedded).

In one embodiment, a plurality of grooves on the inner coating surface of the coating extend in the longitudinal direction of the coating and are located parallel to each other, with a width of 0.5 µm to 200 µm. In one embodiment, the pluralities of grooves on the inner coating surface of the coating have a maximal width of 1 µm to 30 µm. In one embodiment, the plurality of grooves on the inner coating surface of the coating have a maximal width of 2 µm to 15 µm, in particular 2 µm to 5 µm.

In one embodiment, the pluralities of grooves on the inner coating surface of the coating have a maximal width of 80 µm to 120 µm. In one embodiment, the pluralities of grooves on the inner coating surface of the coating have a maximal width of approximately 100 µm.

In one embodiment, the plurality of grooves on the inner coating surface of the coating have a maximal width of 1 µm to 6 µm, in particular a maximal width of 2 µm to 5 µm. In one embodiment, the pluralities of grooves on the inner coating surface of the coating have a maximal width of approximately 2 µm. The smaller grooves are preferred since this space influences the adhesion of progenitors as this space is congruent with the surface receptor size and leads to forced adhesion.

The maximal width of the grooves is the maximal distance between one side of the groove and the neighboring side of the same groove, measured transverse to the longitudinal extension direction of the sides.

In some embodiments, the grooves comprise a rectangular shape, a semicircle shape or a trapezoid shape. In some embodiments, the corners of the applied shape of the grooves, in particular a rectangular shape or a trapezoid shape, are rounded, allowing for a better laminar flow, which will be discussed below. In some embodiments, the grooves comprise a semicircle shape with a maximal width of 2 µm to 15 µm, in particular 2 µm to 5 µm. In some embodiments, the grooves comprise a rectangular shape with each groove comprising essentially identical maximal widths in the range of 2 µm to 15 µm, in particular 2 µm to 5 µm.

In some embodiments, the grooves comprise an upper width in the range of 2 µm to 15 µm, in particular 2 µm to 5 µm, and a lower width in the range of 50% to 150%, in particular in the range of 80% to 120%, of the size of the upper width. The upper width is the distance between one side of the groove and the neighboring side of the same groove, measured along the circumference of the inner diameter of the inner coating surface of the coating and the lower width is the distance between one side of the groove and the neighboring side of the same groove, measured transverse to the longitudinal extension direction of the sides of the groove and in the plane, in which the bottom of the grooves essentially expands. Thus, the upper width is located near the circumference of the inner diameter of the inner coating surface of the coating and the lower width is located at the bottom of the grooves. In some embodiments, the grooves comprise a rectangular shape, a semicircle or trapezoid shape with an upper width in the range of 2 µm to 15 µm, in particular 2 µm to 5 µm and a lower width in the range of 50% to 150%, in particular in the range of 80% to 120%, of the size of the upper width.

Furthermore, the depth of the grooves, which is the distance from the circumference of the inner diameter of the inner coating surface of the coating to the bottom of the groove, is in the range of 2 µm to 15 µm, in particular 2 µm to 5 µm. In some embodiments, the upper width and the depth of one groove are essentially the same. In some embodiments, the upper and lower width and the depth of one groove are essentially the same.

In some embodiments, the upper and/or lower width and/or depth of neighboring grooves are essentially the same. In some embodiments, neighboring grooves comprise different upper and lower widths and a different depth.

In some embodiments, the distance between neighboring grooves is under 10 µm, in particular under 1 µm. In some embodiments, the distance between two neighboring grooves is essentially identical for the plurality of grooves. The distance between neighboring grooves is the distance between one side of a groove and the neighboring side of a neighboring groove, measured along the circumference of the inner diameter of the inner coating surface of the coating.

Generally, the coating will capture endothelial cells and progenitor cells. These cells will attach themselves on the inner side of the coating. The main part of the captured cells will be progenitor cells, whereby endothelial cells will only be captured in the range of about 1%, since the progenitor cells are easily available and are particularly mobilized after damage to a natural graft occurs. In general, the major part of the progenitor cells, which amounts to about 80%, originate from the periphery of the artificial vascular graft and migrate through the "holes" in the primary scaffold structure material or the semipermeable primary scaffold structure material and the semipermeable coating material (see explanation above) and only a small part (20%) stems from the blood inside the artificial vascular graft. Progenitor cells (from the periphery) originate in general from the adventitia of neighboring tissue (the so called scal+ progenitors). Considering the aorta, most of the cells are encased in the respective wall.

Progenitor cells differentiate either to become endothelial cells or to become smooth muscle cells, depending on the conditions of the blood flow inside the artificial vascular graft. The main conditions governing this differentiation process are the amount of shear stress on a progenitor cell and the amount of turbulent flow inside the artificial vascular graft. The higher the shear stress and the lower the turbulent flow, the higher the probability that a progenitor cell will differentiate to an endothelial cell (which is flat and spindle shaped).

The alignment and the form of the grooves in the longitudinal direction prevents a turbulent flow inside the artificial vascular graft, in particular a turbulent flow directed essentially crosswise to the grooves under conditions of blood flow inside the artificial vascular graft after implantation. Thus, the plurality of grooves comprised in the coating of the inner surface allows for an essentially laminar flow of blood, with no or only a minimum of turbulent flow.

In some embodiments, the shear stress inside the artificial vascular graft is at least 1.5 Pa ($dyn/cm^2$), in particular more than 2.5 Pa ($dyn/cm^2$) under conditions of use of the artificial graft after implantation. Generally, the shear stress on a cell will increase from the position near the inner coating surface of the coating of the artificial vascular graft to the radial center of the artificial vascular graft. Thus, the more a cell is positioned near this center of the artificial vascular graft, the more shear stress will be exerted on this cell. Therefore, the probability of a differentiation to endothelial cells will increase, the nearer a progenitor cell is situated to the radial center of the artificial vascular graft. Cells that are situated with the least distance to the symmetrical center of a tubular shaped artificial vascular graft, will be referred to as luminal cells or cells in luminal position.

Given the combination of the near laminar flow and the shear stress inside the artificial graft captured progenitor cells specifically differentiate to endothelial cells at the luminal position or near the luminal position of the artificial graft and smooth muscle cells at the inner side of the coating. Thus, due to the capturing of progenitor cells and their differentiation, the artificial graft will—after implantation and subsequent differentiation of cells captured onto the graft—comprise smooth muscle cells on the inner coating surface (situated on the primary scaffold structure) and endothelial cells on these smooth muscle cells. Therefore, human endothelial cells are specifically situated in the luminal position of the artificial graft.

Depending on the applied materials for the primary scaffold structure and the coating as well as the shape and diameter of the grooves, the conditions concerning the laminar flow and the shear stress can be selected in order to control the amount of endothelial cells and smooth muscle cells. In some embodiments, the ratio of endothelial cells to smooth muscle cells that differentiate from the captured progenitor cells is 2:1 after a period of 3 to 10 days, particularly after about 7 days. In some embodiments, 5% to 15% of smooth muscle cells (positioned directly or at the vicinity of the coating) and 95% to 85% of endothelial cells (positioned directly or at the vicinity of the luminal position) will differentiate from the captured progenitor cells.

In general, after 30 min progenitor cells are being captured on the inner coating surface of coating. After 7 days around 60% of the area of the inner coating surface of the coating is colonized. The outer side of the coating will be covered by fibrin and then by fibroblasts containing scar tissue.

In one embodiment, the coating comprises as a coating material Collagen IV or a material with ECM components (extracellular matrix), which allows a high capture rate of endothelial cells and progenitor cells on the inner coating surface of the coating and a differentiation rate of progenitor cells to endothelial cells in a rate of essentially 100%.

In one embodiment, the coating comprises as a coating material Collagen IV to enhance cellular migration at the anastomosis site. Thus, the coating comprises as one component Collagen IV. However, it may comprise further components such as cellulose or fibrin for providing an additional stability and reducing the amount of expensive collagen IV. Alternatively Pluronic F 125 (CAS. No. 9003-11-6) und 2-Octy-Cyanoacrylat (CAS No. 133978-15-1) may be applied. Further examples can be found in the experimental section.

In some embodiments, the coating comprises a structure pattern in form of pores. In some embodiments, such pores have a diameter of 50 nm to 500 nm. In some embodiments, such pores have a diameter of 1 μm to 15 μm. In some embodiments, the coating comprises a structure pattern in form of pores. In some embodiments, such pores have a diameter of 10 nm to 100 nm. The structure pattern allows—aside from the migration ability—for a higher capturing rate of endothelial cells and progenitor cells on the inner coating surface of the coating. In some embodiments, the coating material comprises cellulose with a structure pattern in form of pores.

In some embodiments, the cellulose material of the coating is sterile, inert and comprises semipermeable and anti-thrombogenic abilities, as well as the above mentioned flexibility and compliance, whereby the coating comprises a plurality of grooves on the inner coating surface of the coating with a maximal width in the range of about 1 μm to 50 μm. In some embodiments, the coating consists of cellulose material, derived from the bacteria *Acetobacter*, comprising the previously described features and the primary scaffold structure comprises a shape memory alloy, in particular Nitinol. The primary scaffold structure and the coating comprise a flexibility of 5% to 40%, in particular of 15% to 20%, with respect to the original outer diameter of the primary scaffold structure or the original inner diameter of the coating, and a compliance in the range of 400 to 1000%/2.93 kPa (22 mm Hg), in particular in the range of 600 to 800%/2.93 kPa (22 mm Hg). Additionally, the cellulose can comprise a structure pattern in form of pores.

In one embodiment, the artificial vascular graft comprises a second coating on the inner coating surface of the coating, whereby the second coating comprises a plurality of grooves on the inner second coating surface of the second coating and the inner second coating surface of the second coating is facing towards the inner space of the artificial vascular graft. In one embodiment the second coating is Collagen IV. Reference is made to the above mentioned properties and materials concerning the primary scaffold structure and the coating. In some embodiments, the plurality of grooves are comprised on the inner second coating surface of the second coating and on the inner coating surface of the coating situated on the inner surface of the primary scaffold structure.

In one embodiment, the second coating comprises as a coating material Collagen IV to enhance cellular migration at the anastomosis site. However, it may comprise further components such as cellulose or fibrin for providing an additional stability and reducing the amount of expensive collagen IV.

The second coating may be applied in form of a spray comprising an amount of 90% Collagen IV and Fibrin, whereas the remaining 10% may be chosen from a Vascular Endothelial Growth Factor (VEGF) and Penicillin Streptomycin (Pen/Strep), or a suitable comparable material. The 90% of Collagen IV and Fibrin may comprise 20-40% Collagen IV and 70% to 50% Fibrin, in particular 25-35% Collagen IV and 65% to 55% Fibrin, more particularly approximately 30% Collagen IV and approximately 60% Fibrin. Alternatively Pluronic F 125 (CAS. No. 9003-11-6) und 2-Octyl-Cyanoacrylat (CAS No. 133978-15-1) instead of fibrin may be applied.

Further examples can be found in the experimental section.

In some embodiments, the second coating comprises a thickness (whereby thickness is the difference between the inner diameter of the second coating and the inner diameter of the coating) in the range of 0.5 mm to 5 mm, in particular in the range of 1 mm to 2 mm. The inner diameter of the second coating is the maximal distance of two points situated on the inner coating surface of the tubular second coating, measured through the center of the tubular second coating and in the plane, which extends vertical to the longitudinal extension direction of the tubular second coating.

In one embodiment, the primary scaffold structure comprises a shape memory alloy with 50 to 60% Nickel (Reference) and 40-50% Titanium (Balance), in particular 54.5% to 57.0% Nickel (Reference) and 43.0-45.5% Titanium (Balance) according to the Standard Specification for Wrought Nickel-Titanium Shape Memory Alloys for Medical Devices and Surgical Implants (ASTM F2063-05; Nitinol) and the coating material comprises cellulose material. According the characteristics and functions of the primary scaffold structure and the coating in form of cellulose material reference is made to the above mentioned details. Additionally, the artificial vascular graft comprises a second coating on the Inner coating surface of the coating with Collagen IV as a second coating material, whereby the second coating comprises a plurality of grooves on the inner second coating surface. In an alternative, the coating and the second coating comprise a plurality of grooves on their inner surfaces. This allows for, if the artificial vascular graft is used as intended, a high capture rate of endothelial cells and progenitor cells on the inner second coating surface of the second coating and a differentiation rate of progenitor cells to endothelial cells in a rate of essentially 100%, as discussed above. Reference is also made to the above-mentioned properties concerning the plurality of grooves By using an artificial vascular graft as intended an essentially laminar flow and a shear stress of at least 1.5 Pa (dyn/cm$^2$), in particular more than 2.5 Pa, is achieved. The applied primary scaffold, the coating as well as the plurality of grooves allow that a specific amount of smooth muscle cells could be differentiated and attached to the inner coating surface of the coating, namely 5% to 40%, in particular 5% to 15%, whereby the rest of the progenitor cells are differentiated to human endothelial cells and are situated in or near the luminal position. Therefore, it is possible to accumulate only specific types of cells, namely human endothelial cells (as a major part) in the luminal position, as well as smooth muscle cells in a specific and restricted amount near the inner coating surface of the coating or the inner second coating surface of the second coating. Those cells provide very similar conditions compared to a human blood vessel inside the artificial graft.

By the in-vivo capturing and/or differentiation of endothelial cells a functional endothelium is provided in the luminal position with anti-thrombogenic properties. Due to tight intercellular connections, the provided endothelium works as a semi-selective barrier between the lumen of the artificial vascular graft and surrounding tissue, controlling the passage of materials and the transit of white blood cells into and out of the bloodstream.

Thus, the artificial graft, if is used as intended, is colonized in-vivo by the desired cells derived from the human body. There is no requirement for an external incubation or cell donation, which comprise an infection and repulsion risk. The artificial vascular graft could be used without a time delay and is compatible for every patient.

The artificial vascular grafts according to the invention comprise similar blood vessel qualities as a human blood vessel, including an appropriate physiological compliance and burst pressure in order to withstand hemodynamic pressure changes without failure and provide an appropriate response to physiological changes. These artificial vascular grafts are highly compatible for each patient without the need for additional medication, easy of use for the physician and comprise further an unproblematic storage and rapid availability. The artificial vascular graft comprises antithrombogenic and non-immunogenic properties and is resistant to infection. Furthermore, the in-vivo provision of a functional endothelium provides an integration of the artificial vascular graft into the vascular system without resulting in chronic inflammation, hyperplasia or fibrous capsule formation or thrombosis.

According to a second aspect the invention relates a method for production of an artificial vascular graft, in particular an artificial vascular graft according to any one of claims 1 to 11, which is characterized by the following steps:
  a. providing a bioreactor comprising a cellulose producing bacteria;
  b. introducing a tubular primary scaffold structure into the bioreactor, whereby said tubular primary scaffold structure encompasses an inner space, and said primary scaffold structure has an inner surface facing towards said inner space;
  c. introducing a tubular structural component into said inner space, whereby the distance between said inner surface and the perimeter of said tubular structural component is in the range of 0.5 mm to 6 mm, whereby said tubular structural component comprises protruding structural elements, which are situated on the perimeter of said tubular structural component and extend along the longitudinal extension direction of said tubular structural component, whereby said protruding structural elements comprise a height in the range of about of 2 µm to 15 µm and a width in the range of about 1 µm to 50 µm;
  d. covering of the primary scaffold structure with cellulose providing a coating;
  e. removal of the structural component from the primary scaffold structure.

In one embodiment, the cellulose producing bacteria is provided in a liquid bacteria medium.

In some embodiments, the tubular primary scaffold structure and the tubular structural component are encompassed by the liquid bacteria medium (e.g. by a vertical application). In some embodiments, the tubular primary scaffold structure and the tubular structural component can be in contact with pure oxygen (e. g by bubbling through the liquid media).

In one embodiment, the tubular primary scaffold structure and the tubular structural component are provided in a horizontal setting—with respect to the surface of the liquid bacteria medium, whereby parts of the tubular primary scaffold structure and the tubular structural component are encompassed by the liquid bacteria medium and parts are encompassed by air. In some embodiments approximately 50% of the tubular primary scaffold structure and the tubular structural component are encompassed by the liquid bacteria medium.

In some embodiments, the contact of said parts of the tubular primary scaffold structure and the tubular structural component with the liquid bacteria medium and the air is changed periodically, in particular by a rotating system attached to the tubular primary scaffold structure and the tubular structural component.

In some embodiments, the rotation is set to 1 to 10 rounds per minute (rpm), in particular to 3 rpm to 8 rpm, more particularly to approximately 6 rpm. A continuous rotation is preferred, providing a more evenly distribution of said cellulose.

In some embodiments, the temperature of the liquid bacteria medium and the bioreactor is 26-28° Celsius.

In some embodiments, the culture time is in the range of 1 to 10 days, in particular approximately 2 to 8 days, more particularly approximately 4 days.

The liquid bacteria medium may be exchanged if appropriate, in particular every 24 hours.

In some embodiments, the air in the bioreactor comprises an enhanced amount of oxygen (more than 21%).

In some embodiments, the oxygen content in the air in the bioreactor is enhanced by a periodical addition of pure oxygen, in particular pure oxygen with an oxygen content of 99.5%, 99.95%, 99.995% or 99.999%. In some embodiments, the oxygen content in the air in the bioreactor is enhanced by a periodical addition of pure oxygen every 6 hours. A preferred level of oxygen is 65% up to 80% pure oxygen. The use of an enhanced amount of oxygen increases the stability of the cellulose coating. With "normal" air a stability of 26.66 kPa (350 mm Hg) is achieved, whereas the use of an oxygen content of approximately 80% provides a stability of 133.32 kPa (1000 mm Hg).

The cellulose produced by the bacteria in the bioreactor will slowly cover the primary scaffold structure and the tubular structural component. After 5 to 7 days the primary scaffold structure, the protruding elements and the perimeter of the tubular structural component are covered by the cellulose coating and the tubular structural component is removed. After removal of the tubular structural component the protruding elements will effect a plurality of grooves—by way of negative impression—in the inner coating surface of the coating, whereby the rest of the inner coating surface of the coating will comprise a tubular surface, due to the growth limitation in form of the perimeter of the tubular structural component.

The distance between the inner surface of the primary scaffold structure to the perimeter of the tubular structural component is measured in the plane, which extends vertical to the longitudinal extension direction of the primary scaffold structure. Thus, depending on the location of the symmetrical center of the tubular structural component and the symmetrical center of the primary scaffold structure, the distance between the inner surface of the primary scaffold structure to the perimeter of the tubular structural component may be different, viewed along the circular path of the primary scaffold structure.

In one embodiment, the tubular structural component is placed inside the primary scaffold structure, in such a way, that the symmetrical center of the tubular structural component and the symmetrical center of the primary scaffold structure are congruent. Thus, the distance between the inner surface of the primary scaffold structure to the perimeter of the tubular structural component is essentially the same, viewed along the circular path of the primary scaffold structure. In other words, the symmetrical center of the tubular primary scaffold structure and the tubular structural component are essentially in the same place.

The main body of the tubular structural component, comprising a defined outer diameter, is viewed as the perimeter of the tubular structural components. The protruding structural components, which are situated on the perimeter of the tubular structural component, are not relevant in view of the above discussed distance. Thus, after coating of the primary scaffold structure with cellulose, the inner diameter of the coating will be restricted by the outer diameter of the structural component. Depending on the applied diameter of the primary scaffold structure and the desired inner diameter of the coating, as defined above, the outer diameter of the tubular structural component can be chosen accordingly. For example, if a primary scaffold structure with an outer diameter (the thickness of the primary scaffold structure will be neglected in this example) of 6 mm is applied and a coating with an inner diameter of 4 mm is desired, the outer diameter of the tubular structural component will be 2 mm.

Furthermore, the distance from the inner surface of the primary scaffold structure to the perimeter of the tubular structural component will restrict the "inner" thickness of the coating material (measured from the inner surface of the primary scaffold structure towards the inner coating surface of the coating situated on the inner surface of the primary scaffold structure). In one embodiment the "inner" thickness of the coating material is roughly the same as the "outer" thickness—measured from the outer surface of the primary scaffold structure to the outer coating surface of the coating material, situated on the outer surface of the primary scaffold structure. In one embodiment, the "outer" thickness of the coating material is higher than the "inner" thickness.

In one embodiment, the protruding structural elements are protruding radially from the perimeter of the tubular structural component and comprise the shape of protruding tracks, which extend parallel to each other in the longitudinal extension direction of the structural component and comprises a maximal width of about 0.1 µm to 200 µm, in particular 1 µm to 50 µm. In a further embodiment, the protruding tracks on the perimeter of the tubular structural component have a maximal width of 1 µm to 30 µm. In one embodiment, the protruding tracks on the perimeter of the tubular structural component have a maximal width of 2 µm to 15 µm, in particular 2 µm to 5 µm. The maximal width of the protruding tracks on the perimeter of the tubular structural component is the maximal distance between one side of the protruding tracks and the neighboring side of the same protruding tracks, measured transverse to the longitudinal extension direction of the sides.

In some embodiments, the protruding tracks comprise a rectangular shape, a semicircle shape or a trapezoid shape. In some embodiments, the corners of the applied shape of the protruding tracks, in particular a rectangular shape or a trapezoid shape, are rounded. In some embodiments, the protruding tracks comprise a semicircle shape with a maximal width of 2 µm to 15 µm, in particular 2 µm to 5 µm. In some embodiments, the protruding tracks comprise a rectangular shape with a maximal width in the range of 2 µm to 15 µm, in particular 2 µm to 5 µm.

In some embodiments, the protruding tracks comprise a first width in the range of 2 µm to 15 µm, in particular 2 µm to 5 µm, and a second width in the range of 50% to 150%, in particular in the range of 80% to 120%, of the size of the first width. The first width is the distance between one side of a protruding track and the neighboring side of the same protruding track, measured along the circumference of the outer surface of the tubular structural component and the second width is the distance between one side of a protruding track and the neighboring side of the same protruding track, measured transverse to the longitudinal extension direction of the sides of the protruding track and in the plane, which expands through the points of the protruding track, which are situated furthest from the perimeter of the structural component. In some embodiments, the protruding tracks comprise a rectangular shape, a semicircle or trapezoid shape with a first width in the range of 2 µm to 15 µm, in particular 2 µm to 5 µm and a second width in the range of 50% to 150%, in particular in the range of 80% to 120%, of the size of the first width.

Furthermore, the height of the protruding tracks, which is the distance from the perimeter of the tubular structural component to the point of the protruding track, which is situated furthest from the perimeter of the tubular structural component (in other words, the top of the protruding track), measured transverse to the longitudinal extension direction of the tubular structural component, is in the range of 2 µm to 15 µm, in particular 2 µm to 5 µm. In some embodiments, the first width and the height of one protruding track are essentially the same. In some embodiments, the first and second width and the height of one protruding track are essentially the same.

In one embodiment, the protruding tracks of the tubular structural component comprise a length in their longitudinal extension direction in the range of at least the length of the primary scaffold structure.

In one embodiment, the tubular structural component is removed by applying a force on the tubular structural component, whereby the force is directed essentially along the longitudinal extension direction of the primary scaffolds structure. Thus, the tubular structural component is removed along the longitudinal extension direction of the primary scaffolds structure.

In one embodiment, the outer diameter of the tubular structural component is variably adjustable, in such a way that before the removal of the structural component the outer diameter of the structural component is minimized, so that the protruding elements of the tubular structural component are removed vertical to the longitudinal extension direction of the tubular structural component from the coating material. The tubular structural component is subsequently removed along the longitudinal extension direction of the primary scaffold structure, as discussed above. Thus, the structural component could be removed without further contacting the coating material.

In one embodiment, a second coating is applied to the cellulose coating on the inner surface of said cellulose coating which comprises as a coating material Collagen IV to enhance cellular migration at the anastomosis site. Furthermore, the second coating may comprise further components such as fibrin for providing an additional stability. Further examples can be found in the experimental section. The second coating may be applied in form of a spray.

In some embodiment, said spray may be applied after implantation of the graft and completion of the anastomosis.

In one embodiment, the structural component can comprise the form of a rod or a mandrel containing the protruding elements on the outer surface (perimeter) of the rod or mandrel.

Generally, any biologically acceptable material with the ability to be shaped into a tubular structure having the required compliance and flexibility—as discussed above—can be used for the primary scaffold.

In one embodiment, the primary scaffold structure comprises or consists of a metal, a metal alloy, in particular a shape memory alloy, as discussed above.

In some embodiments, the primary scaffold structure comprises or consists of a fibroblast sheet. In some embodiments, the primary scaffold structure comprises or consists of an arterial, respectively venous decelluarized homograft or xenograft.

In some embodiments, the primary scaffold structure comprises or consists of a blostable polymeric material or a degradable polymer material, whereby the polymer could be a synthetic polymer or a biopolymer. Reference is made to the previous discussion of these materials.

In one embodiment, the primary scaffold structure comprises or consists of a structured surface in form of a mesh structure. In some embodiments, the primary scaffold structure comprises a knitted, braided or woven mesh structure or a wire mesh structure, as discussed above.

In some embodiments, the primary scaffold structure comprises or consists of a shape memory polymer or an elastomeric synthetic polymer, as discussed above.

In one embodiment, the primary scaffold structure consists of a wire mesh structure, as discussed above. Due to the "holes" of the wire mesh structure, the cellulose will not only cover the primary scaffold structure, but also grow through the "holes" of the wire mesh, providing a strong connection between the primary scaffold structure and the cellulose coating.

In one embodiment, the primary scaffold structure consists of a wire mesh structure having a shape memory alloy as a primary scaffold structure material with 50 to 60% Nickel (Reference) and 40-50% Titanium (Balance), in particular 54.5% to 57.0% Nickel (Reference) and 43.0-45.5% Titanium (Balance) according to the Standard Specification for Wrought Nickel-Titanium Shape Memory Alloys for Medical Devices and Surgical Implants (ASTM F2063-05; Nitinol). According the characteristics and functions of the primary scaffold structure reference is made to the above mentioned details.

In one embodiment, the cellulose is derived from the bacteria *Acetobacter* and is sterile, inert and comprises semipermeable and anti-thrombogenic abilities, as well as the above discussed flexibility and compliance.

In one embodiment, the cellulose is derived from the bacteria *Acetobacter* and the primary scaffold structure consists of a wire mesh structure having a shape memory alloy as a primary scaffold structure material with 50 to 60% Nickel (Reference) and 40-50% Titanium (Balance), in particular 54.5% to 57.0% Nickel (Reference) and 43.0-45.5% Titanium (Balance) according to the Standard Specification for Wrought Nickel-Titanium Shape Memory Alloys for Medical Devices and Surgical Implants (ASTM F2063-05; Nitinol). According the characteristics and functions of the primary scaffold structure reference is made to the above mentioned details.

In one embodiment, the cellulose is derived from the bacteria *Acetobacter*, in particular *Acetobacter xylinum* strain ATTC 23769 and is sterile, inert and comprises semipermeable and anti-thrombogenic abilities, as well as the above discussed flexibility and compliance.

Experimental Section:

Glucosemedia: *Acetobacter Xylinum* Medium with Glucose 2.381% for Production of Cellulose

TABLE 1

| components | percentage | MW | base g/ 1 L | base g/ 2 L | base mg/ 1 L | base mg/ 2 L |
|---|---|---|---|---|---|---|
| KH$_2$PO$_4$ | 0.7 | | 7.00 g | 14.00 g | | |
| MgSO$_4$ × 7 H$_2$O | 0.213 | | 2.13 g | 4.26 g | | |
| H$_3$BO$_3$ | 0.00043 | | 0.0043 | 0.0086 | 4.3 mg | 8.6 mg |
| Nicotinamide | 0.00007 | | 0.0007 | 0.0014 | 0.7 mg | 1.4 mg |
| FeSO$_4$ × 7 H$_2$O | 0.00095 | | 0.010 | 0.019 | 9.5 mg | 19.0 mg |
| Na$_2$HPO$_4$ | 0.134 | 142 | 1.34 g | 2.68 g | | |
| (NH$_4$)$_2$SO$_4$ | 0.354 | | 3.54 g | 7.08 g | | |
| Ethanol abs | 0.473 | | 4.73 ml | 9.46 ml | | |
| Glucose 50% | 2.381 | | 50 ml | 100 ml | | |

Start a Glucose 50%: 125 g in 250 ml MilliQ H$_2$O, filter sterile; Start a saline solution, store overnight in the cold storage room. Add ethanol directly before autoclaving. Add the 50% Glucose solution after the autoclaving to the RT warm medium; KH$_2$PO$_4$—potassium dihydrogen orthophosphate (purum, Fluka, ref. nr. 60230); MgSO$_4$ × 7 H$_2$O—magnesia sulphate heptahydrate (Fluka, ref. nr. 63142); H$_3$BO$_3$—boracic acid (Fluka, ref. nr. 15660); Nicotinamide (cell culture tested, Sigma, ref. nr. N0636-100G); FeSO$_4$ × 7 H$_2$O—Ferrous sulphate Heptahydrat (Sigma, ref. nr. F8633-250G); Na$_2$HPO$_4$—disodium hydrogen phosphate (Sigma, ref. nr. S3264-500G); (NH$_4$)$_2$SO$_4$—Ammonium sulphate (Fluka, ref. nr. 09980); ethanol absolute (>99.8%), Fluka, ref. nr. 02860), the substances are dissolved in MilliQ H$_2$O (ISO 696).

Bacteriamedia: Starter Medium *Actobacter xylinum*

TABLE 2

Dissolve components/ingredients successively in MilliQ H$_2$O and then it has to be filled in glass bottles and to be autoclaved (20 min. 121° C.).

| | % | MW | 1 L | 2 L |
|---|---|---|---|---|
| D(+) glucose waterfree Sigma | 2 | 180.16 | 20 g | 40.0 g |
| proteose peptone Fluka, ref. nr. 29185-500G-F | 0.5 | | 5.0 g | 10.0 g |
| yeast extract: Sigma, ref. nr. Y1625-250G | 0.5 | | 5.0 g | 10.0 g |
| Na$_2$HPO$_4$ Sigma, ref. nr. S3264-500G | 0.27 | 142 | 2.7 g | 5.4 g |
| Citric acid Sigma, ref. nr. C2404-100G | 0.15 | | 1.5 g | 3.0 g |

Example Concerning the Provision of a Cellulose Coating:

Provision of a bioreactor comprising a cellulose producing bacteria in a liquid bacteria medium according to the above mentioned tables (500 ml of liquid *Acetobacter* media). A tubular primary scaffold structure in form of a nitinol mesh is provided on a tubular structural component (mandril), with protruding structural elements. Both are arranged horizontally to the liquid media on the surface of said media in such a way that approximately 50% of the mandril and the mesh are encompassed by the liquid bacteria medium and both are arranged rotatable in the bioreactor on a rotating.

By rotating the mandril and the mesh (with 6 rpm) parts of the mandril and the mesh are contacting the liquid bacteria medium and air periodically. The oxygen content in the air in the bioreactor is enhanced by a periodical addition of pure oxygen every 6 hours.

The temperature of the liquid bacteria medium and the bioreactor is 26-28° Celsius.

The media change every 24 hours and the mandril and the mesh are rotated for 4 days, providing a providing a coating.

After that, the mandril is removed providing a cellulose coating on the mesh, which comprises grooves on the inner surface by way of negative impression.

Second Coating:

The second coating may be applied in form of a spray, in particular after implantation of the graft and completion of the anastomosis, to enhance cellular migration at the anastomosis site and if additional stability is required. The spray may contain:

Fibrin 60%, Collagen IV 30% and the remaining 10% comprise VEGF (Vascular Endothelial Growth Factor) 25 ng/ml and 200 U/ml Pen/Strep (Penicillin Streptomycin "Pen/Strep" mixtures contain 5,000 units of penicillin (base) and 5,000 µg of streptomycin (base)/ml utilizing penicillin G (sodium salt) and streptomycin sulfate in 0.85% saline.)

The invention is further illustrated by the following figures and examples, from which further advantages and embodiments can be drawn. The figures and examples are not intended to limit the scope of the claimed invention.

FIGURE LEGENDS

Figure 3:
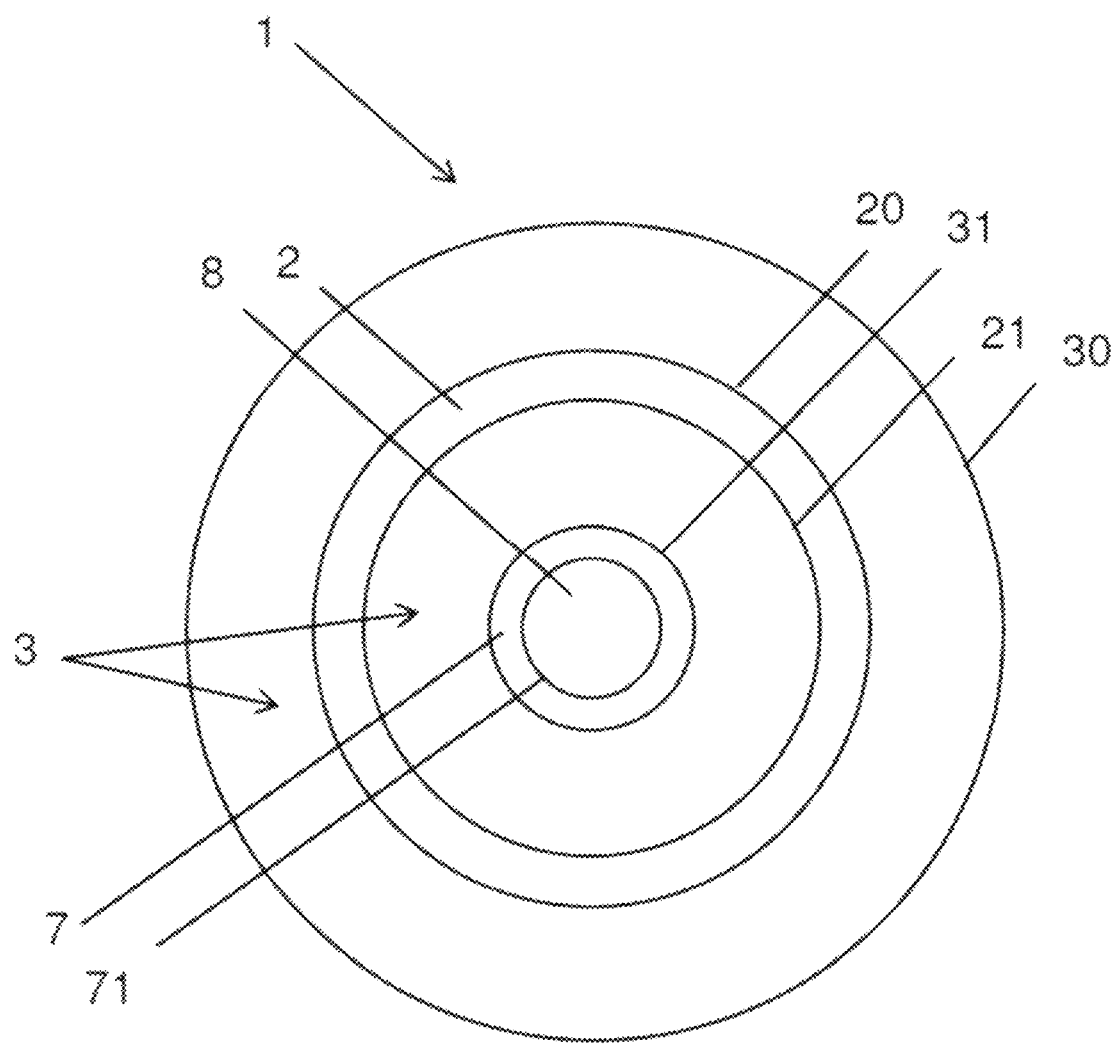
Figure 4:
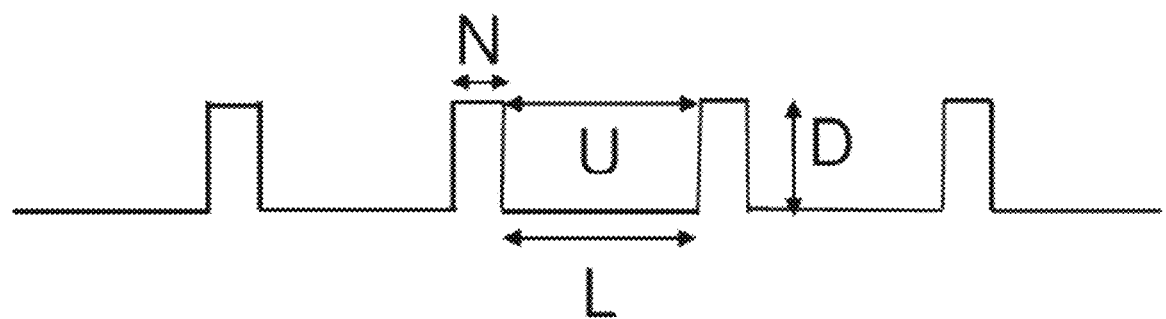
Figure 4:
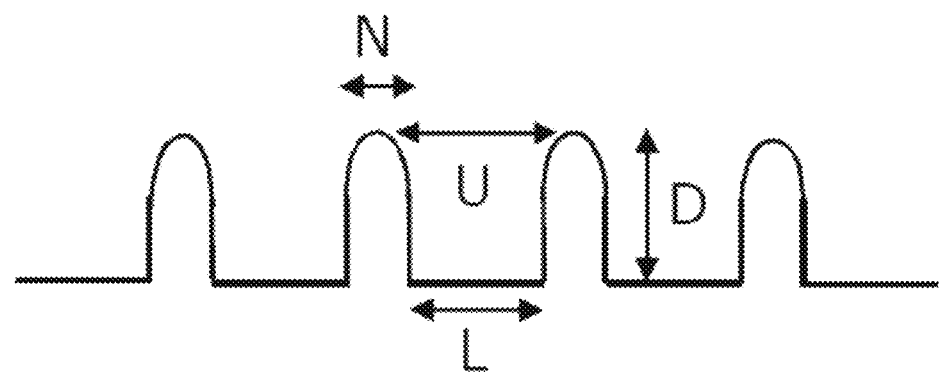
Figure 4C:
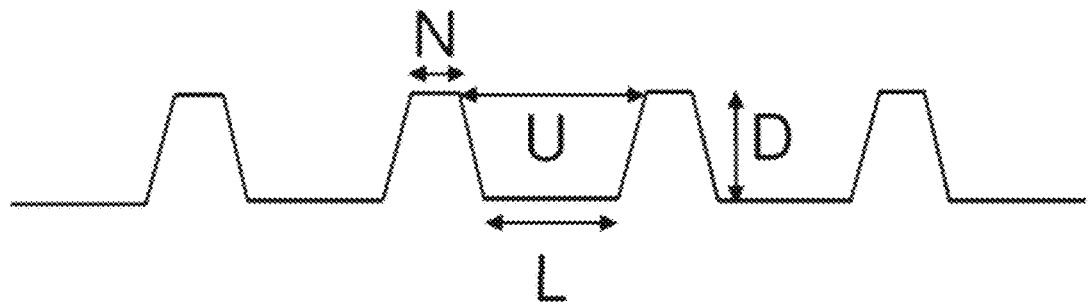
Figure 6:
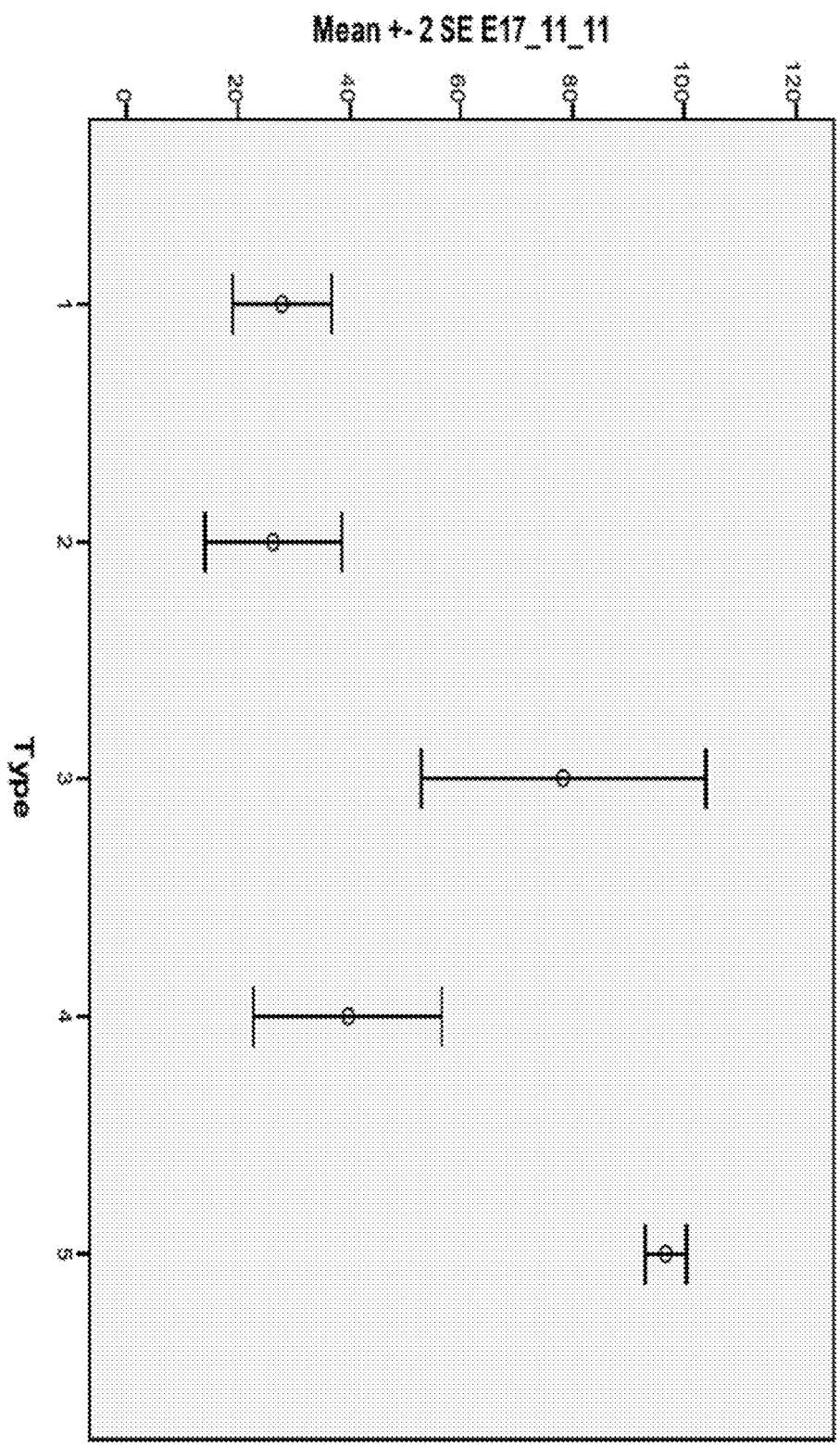

FIG. 1: Shows a schematic cross section view of an artificial vascular graft 1 according to one aspect of the invention;

FIG. 2A: Shows a schematic cross section view of an artificial vascular graft 1 according to a second aspect of the invention;

FIG. 2B: Shows an enhanced schematic cross section view of parts of the coating 3 of the artificial vascular graft 1 of FIG. 2A;

FIG. 3: Shows a schematic cross section view of an artificial vascular graft 1 according to a third aspect of the invention;

FIG. 4 A-C: Show enhanced schematic cross section views of different shapes of the plurality of grooves 4 situated on the inner coating surface 31 of a coating 3;

FIG. 5 A-D: Show enhanced images of the plurality of grooves on the inner coating surface 31 of the coating 3 of an artificial vascular graft 1 in different enhancement levels, whereas A shows grooves with a width of 1 µm (Type 1), B shows grooves with a width of 2 µm (Type 1), C shows grooves with a width of 8 µm (Type 3), D shows grooves with a width of 8 µm (Type 4), whereas visible "dots" are captured cells;

FIG. 6 Shows a diagram concerning the adhesion of cells on the inner coating surface 31 of the coating 3 of an artificial vascular graft 1 measured in minutes (25 endothelial cells per quarter field of view in the microscope) for the types 1, 2, 3, and 4 as depicted in FIG. 5 A to D (x-axis) and type 5 (100 µm width of grooves).

REFERENCE LIST 1 vascular graft
2 primary scaffold structure
20 outer surface of the primary scaffold structure
21 inner surface of the primary scaffold structure
3 coating
30 outer coating surface of the coating
31 inner coating surface of the coating
4 grooves
7 second coating,
71 inner second coating surface of the second coating
8 inner space of the artificial vascular graft
A thickness of the primary scaffold structure
B inner thickness of the coating
C outer thickness of the coating
D depth of the grooves
N distance between neighboring grooves
L lower width of the grooves
U upper width of the grooves
W maximal width of the grooves
X outer diameter of the primary scaffold structure
Y inner diameter of the coating

FIGURES AND EXAMPLES

FIG. 1 shows a schematic cross section view of an artificial vascular graft 1 according to one aspect of the invention.

The artificial vascular graft 1 comprises a primary scaffold structure 2, which encompasses an inner space 8 of the artificial vascular graft 1. The primary scaffold structure 2 has an inner surface 21 facing towards the inner space 8 and an outer surface 20 facing away from the inner space 8. The artificial vascular graft 1 comprises further a coating 3 situated on the inner surface 21 of the primary scaffold structure 2. The coating 3 comprises further an inner coating surface 31 facing towards the inner space 8 of the artificial vascular graft 1. Additionally, the artificial vascular graft 1 comprises a plurality of grooves (not shown due to reasons of clarity; concerning the plurality of grooves on the inner coating surface 31 of the coating 3 reference is made to FIGS. 2A and 2B) in said coating 3, which are situated on the inner coating surface 31 of the coating 3.

The primary scaffold structure 2 and the coating 3 comprise each a symmetrical, tubular shape with identical diameters throughout the tubular artificial vascular graft 1.

The primary scaffold structure 2 comprises a tubular shape with an outer diameter X of about 3 mm for use as a small-size diameter artificial vascular graft 1. The outer diameter X is the maximal distance of two points situated on the outer surface 20 of the primary scaffold structure 2, measured through the center of the tubular primary scaffold structure 2 and in the plane, which extends vertical to the longitudinal extension direction of primary scaffold structure 2, whereby the outer diameter X is depicted in FIG. 1, due to reasons of clarity, slightly above the center of the tubular primary scaffold structure 2. The thickness A of the primary scaffold structure 2 (the difference between the outer diameter X and the inner diameter of the primary scaffold structure 2) is about 0.2 mm. Concerning the outer diameter X and the thickness A of the primary scaffold structure 2, all the previously discussed values may be employed.

The primary scaffold structure 2 comprises an inert, sterile, anti-thrombogenic and semipermeable polymer material. Reference is made to the above discussed polymer materials.

The coating 3 comprises a tubular shape with an inner diameter Y of about 2 mm. The inner diameter Y is the maximal distance of two points situated on the inner coating surface 31 of the tubular coating 3, measured through the center of the tubular coating 3 and in the plane, which extends vertical to the longitudinal extension direction of tubular coating 3. The inner thickness B of the coating 3 (the difference between the inner diameter of the primary scaffold structure 2 and the inner diameter Y of the coating 3) is about 0.8 mm. Concerning the inner diameter Y and the inner thickness B of the coating 3, all the previously discussed values may be employed.

The coating 3 consists of an inert, sterile, anti-thrombogenic and semipermeable polymer material. Reference is made to the above discussed polymer materials.

The primary scaffold structure 2 and the coating 3 comprise a compliance of 600%/2.93 kPa (22 mm Hg), a flexibility of 15% and a burst pressure higher than 133.32 kPa. Other materials with a compliance and flexibility according to the above discussed characteristics may be applied.

Therefore, the primary scaffold structure 2 and the coating 3 comprise similar mechanical properties as the native counterpart and provide a response to physiological changes by means of adequate vasoconstriction and relaxation, if it is used as intended. They function without undue bulging or aggravated mismatching phenomena leading to graft failure. Concerning the characteristics of the grooves 4, reference is made to the discussion of FIGS. 2A and 2B.

FIGS. 2A and 2B show a schematic cross section view of an artificial vascular graft 1 according to a second aspect of the invention and an enhanced schematic cross section view of the coating 3 of the artificial vascular graft 1 of FIG. 2A comprising a plurality of grooves 4.

The artificial vascular graft 1 comprises a tubular primary scaffold structure 2, which encompasses an inner space 8 of the artificial vascular graft 1. The maximal width of the grooves primary scaffold structure 2 has an inner surface 21 facing towards the inner space 8 and an outer surface 20 facing away from the inner space 8. The artificial vascular graft 8 comprises further a coating 3, which encloses the primary scaffold structure 2. The coating 3 comprises an inner coating surface 31 facing towards the inner space 8 of the artificial vascular graft 1 and an outer coating surface 30 facing away from the inner space 8 of the artificial vascular graft 1.

Additionally, the artificial vascular graft 1 comprises a plurality of grooves 4 (which will be shown in FIG. 2B) in the coating 3, which are situated on the inner coating surface 31 of the coating 3.

The primary scaffold structure 2 and the coating 3 comprise each a symmetrical tubular structure with identical diameters throughout the tubular artificial vascular graft 1.

Figure 2:
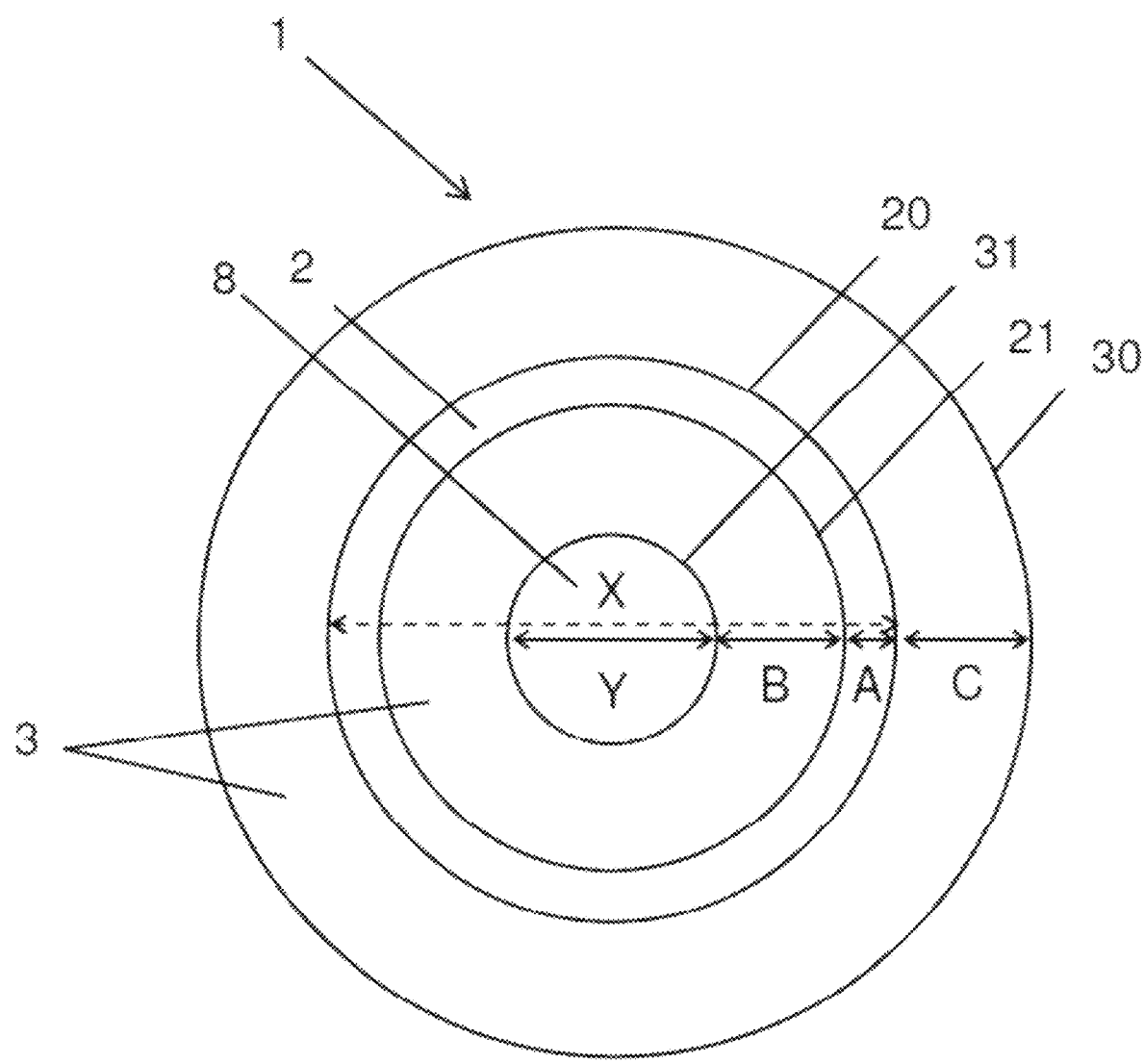
Figure 2:
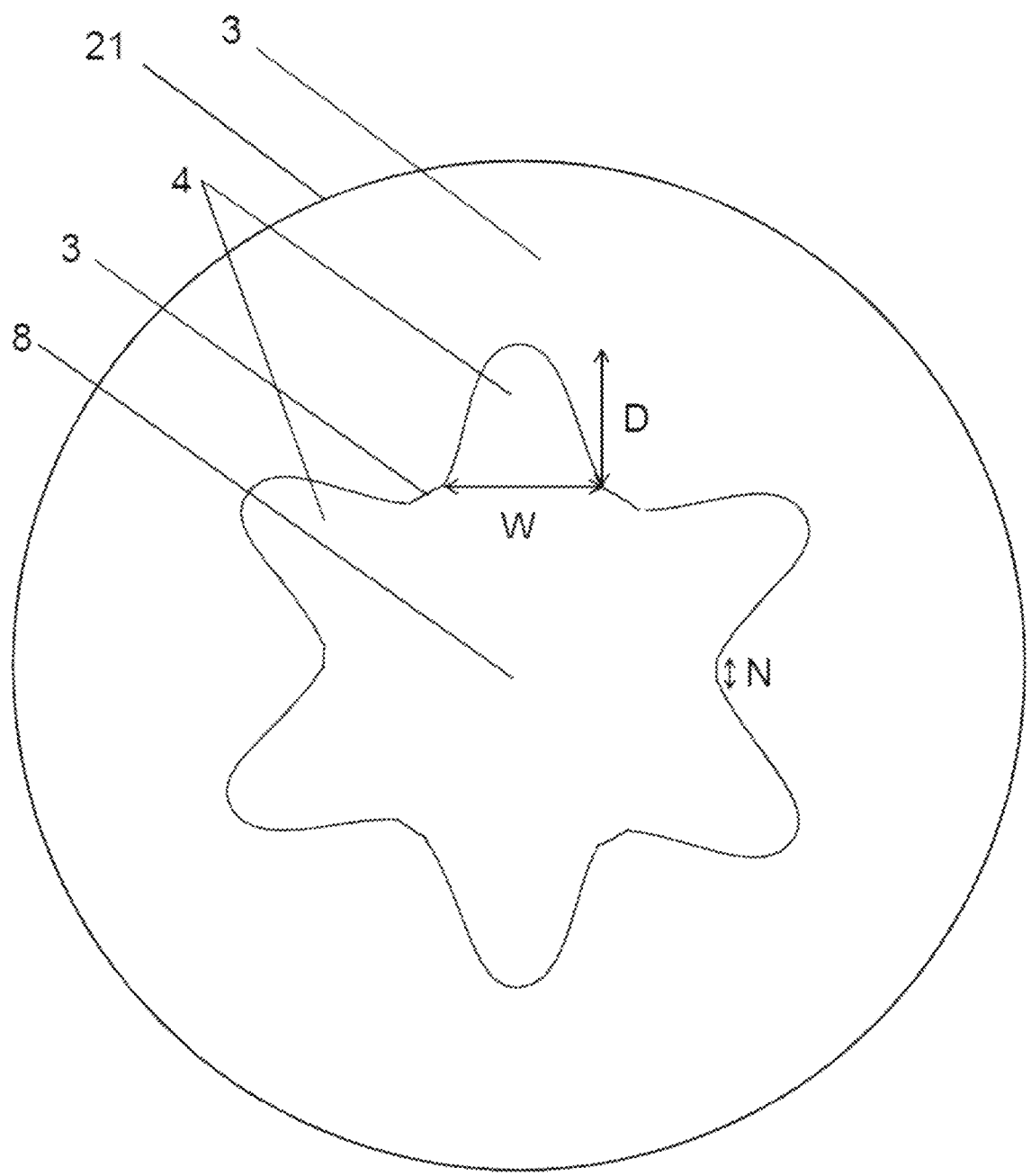

The primary scaffold structure 2 comprises a tubular shape with an outer diameter X (as defined previously) of about 4 mm for use as a small-size diameter artificial vascular graft 1, whereby the outer diameter X is depicted in FIG. 2, due to reasons of clarity, slightly above the center of the tubular primary scaffold structure 2. The thickness A of the primary scaffold structure 2 (the difference between the outer diameter X and the inner diameter of the primary scaffold structure 2) is about 0.2 mm. Concerning the outer diameter X and the thickness A of the primary scaffold structure 2, all the previously discussed values may be also employed.

The coating 3 comprises a tubular shape with an inner diameter Y (as defined previously) of about 2.5 mm. The inner thickness B (the difference between the inner diameter of the primary scaffold structure 2 and the inner diameter Y of the coating 3) and the outer thickness C of the coating 3 (the difference between the outer diameter X of the primary scaffold structure 2 and the outer diameter of the coating 3) is about 0.8 mm. Different values of the inner diameter Y, inner thickness B and outer thickness C of the coating 3 may be applied.

The primary scaffold structure 2 consists of a Nitinol-mesh with flexibility of 20%, compliance in the range of 700%/2.93 kPa (22 mm Hg) and burst pressure higher than 133.32 kPa. The Nitinol mesh comprises a wire mesh structure, whereby the maximal distance between neighboring wires ranges from about 35 µm to 50 µm. Thus, the wire mesh structure provides "holes" in the surface with an area of up to 2 500 µm$^2$. Other materials or other wires with different characteristics, as previously discussed, may be applied.

The coating 3 consists of an inert, sterile, anti-thrombogenic and semipermeable cellulose, derived from the bacteria *Acetobacter*. The coating 3 comprise further a compliance of 700%/2.93 kPa, a flexibility of 20% and a burst pressure higher than 133.32 kPa. Other materials with a compliance and flexibility according to the above discussed characteristics may be applied. Thus, the coating material is compatible for every patient and there is no need for additional anticoagulation and the artificial vascular graft is able to recoil in order to prevent aneurysm formation and exhibits a physiological compliance comparable to a native vessel in order to withstand hemodynamic pressure changes without failure, if the artificial vascular graft is used as intended.

The flexibility of the primary scaffold structure 2 and the coating 3 allow a shear stress of more than 2.5 Pa, if the artificial vascular graft is used as intended. Reference is made to the previous discussion for further details.

Therefore, the primary scaffold structure 2 and the coating 3 comprise similar mechanical properties as the native counterpart and provide a response to physiological changes by means of adequate vasoconstriction and relaxation, if it is used as intended. They function without undue bulging or aggravated mismatching phenomena leading to graft failure.

Furthermore, the cellulose material of the coating 3 reaches through the "holes" of the mesh structure of the primary scaffold structure 2 allowing a strong connection between the primary scaffold structure 2 and the coating 3. Thus, providing a necessary stability after a potential cutting of the artificial vascular graft 1 (no parts of the mesh of the primary scaffold structure will come in contact with living tissue, due to the coating 3, in which the primary scaffold structure 2 is completely embedded).

Additionally, the mesh structure of the primary scaffold structure 2 and the semipermeable cellulose material of the coating 3 allow, if the graft is used as intended, only a migration of a specific type of cells and gases from the outside of the artificial vascular graft 1 to the inner space 8 of the artificial vascular graft 1. Particularly $O_2$ and $CO_2$, vascular growth factors, all humoral agents, progenitor cells capable of differentiating towards endothelial lineages and macrophages, are allowed to migrate through the primary scaffold structure 2 and the coating 3 to the inner coating surface 31 of the coating 3, whereby the coating 3 remains impermeable for the remaining substances of blood. Thus, the coating 3 functions as a selective barrier inside the artificial vascular graft 1.

Furthermore, the inner coating surface 31 of the coating 3 comprises a plurality of grooves 4 (FIG. 2B), which extend along the longitudinal extension direction of the tubular coating 3 and are located parallel to each other. The number or the grooves is only a schematic example, due to clarity reasons.

The plurality of grooves 4 on the inner coating surface 31 of the coating 3 have a maximal width W of about 5 µm. The maximal width W of the grooves 4 is the maximal distance between one side of the groove 4 and the neighboring side of the same groove 4, measured transverse to the longitudinal extension direction of the sides. Furthermore, the depth D of the grooves 4, which is the distance from the circumference of the inner coating surface 31 of the coating 3 to the bottom of the groove 4, is about 2 μm. The distance N between neighboring grooves is about 1 μm. The distance N between neighboring grooves is the distance between one side of a groove and the neighboring side of a neighboring groove, measured along the circumference of the inner coating surface 31 of the coating 3.

If the artificial vascular graft 1 is used as intended, progenitor cells and endothelial cells (in a small amount) are captured at the inner coating surface 31 of the coating 3. Progenitor cells differentiate to endothelial or smooth muscle cells depending on the conditions inside the artificial vascular graft 1. Two of the main conditions are the shear stress on a progenitor cell and the amount of turbulent flow inside the artificial vascular graft 1. Reference is made to the previous discussion for further details.

The alignment and the form of the groves 4 in the longitudinal direction (in other words in the direction of the blood flow) prevents a turbulent flow inside the artificial vascular graft 1, in particular a turbulent flow, which is directed essentially crosswise to the grooves 4.

In general, the higher the shear stress and the lower the turbulent flow, the higher the chances that a progenitor cell will differentiate to an endothelial cell. On the other hand, the more turbulent flow resides inside the artificial vascular graft 1 and the lower the shear stress on the progenitor cells, the higher the chances that the differentiation to smooth muscle cells occurs. Given the combination of the near laminar flow and the shear stress on the progenitor cells at the luminal position or near the luminal position, the progenitor cells in these positions will differentiate to endothelial cells, whereby the progenitor cells near the coating 3 will differentiate to smooth muscle cells, due to the lower shear stress.

The artificial vascular graft 1 of FIGS. 2A and 2B allows, if it is used as intended, that around one third smooth muscle cells (positioned directly or at the vicinity of the coating) and two thirds of endothelial cells (positioned directly or at the vicinity of the luminal position) will differentiate from the captured progenitor cells after a period of 3 to 10, particularly 7 days.

By the in-vivo capturing and/or differentiation of endothelial cells a functional endothelium is provided in the luminal position with anti-thrombogenic properties. Due to tight intercellular connections, the provided endothelium works as a semi-selective barrier between the lumen of the artificial vascular graft and surrounding tissue, controlling the passage of materials and the transit of white blood cells into and out of the bloodstream. The artificial vascular graft 1 could be used without a time delay and is compatible for every patient and comprise similar blood vessel qualities as a human blood vessel, including an appropriate physiological compliance, flexibility and burst pressure in order to withstand hemodynamic pressure changes without failure and provides an appropriate response to physiological changes and anti-thrombogenic and non-immunogenic properties. The artificial vascular graft 1 comprises an unproblematic storage and rapid availability.

FIG. 3 shows a schematic cross section view of an artificial vascular graft according to a third aspect of the invention. The artificial vascular graft 1 of FIG. 3 is similar to the previously discussed artificial vascular graft 1 of FIGS. 2A and B. Reference is made to the details discussed in FIGS. 2A and 2B.

The main difference is, that the artificial vascular graft 1 of FIG. 3 comprises a second coating 7, consisting of Collagen IV, on the inner coating surface 31 of the coating 3, whereby the second coating 7 comprises a plurality of grooves 4 (not shown for reasons of clarity) on the inner second coating surface 71 of the second coating 7 and the inner second coating surface 71 of the second coating 7 is facing towards the inner space 8 of the artificial vascular graft 1.

Collagen IV as a second coating 7 material allows for, if the artificial vascular graft is used as intended, a high capture rate of endothelial cells and progenitor cells on the inner second coating surface 71 of the second coating 7 and a differentiation rate of progenitor cells to endothelial cells in a rate of essentially 100%, as discussed above. Reference is made to the previously discussed properties concerning the plurality of grooves.

FIG. 4 A-C show enhanced schematic cross section views of different shapes of the plurality of grooves 4 situated on the inner coating surface 31 of a coating 3.

FIG. 4 A shows a plurality of grooves 4 with a rectangular shape. The grooves 4 comprise an upper width U in the range of 2 μm to 15 μm, in particular 2 μm to 5 μm. The upper width U is the distance between one side of a groove 4 and the neighboring side of the same groove 4, measured along the circumference of the inner coating surface 31 of the coating 3, and a lower width L, which is located at the bottom of a groove 4 and measured transverse to the longitudinal extension direction of the sides of the groove and in the plane, in which the bottom of the groove 4 expands. The lower width L is in the range of 50% to 150%, in particular in the range of 80% to 120%, of the size of the upper width U. The depth D of the grooves 4, which is the distance from the circumference of the inner coating surface 31 of the coating 3 to the bottom of the groove 4, is in the range of 2 μm to 15 μm, in particular 2 μm to 5 μm. The distance N between neighboring grooves is under 10 μm, in particular under 1 μm. The distance N between neighboring grooves is the distance between one side of a groove 4 and the neighboring side of a neighboring groove 4', measured along the circumference of the inner coating surface 31 of the coating 3.

FIG. 4 B shows a plurality of grooves 4 with a partially rounded, rectangular shape. Concerning the definition and the parameters of the upper width U, lower width L, depth D and distance N, reference is made to the description of FIG. 4 A.

FIG. 4 C shows a plurality of grooves 4 with a trapezoid shape. Concerning the definition and the parameters of the upper width U, lower width L, depth D and distance N, reference is made to the description of FIG. 4 A.

FIG. 4 A-C show only examples. Different shapes may be applied. Furthermore, the upper and/or lower width and/or depth of neighboring grooves can be essentially the same. Some grooves may comprise different upper and/or lower width and/or depth than a neighboring groove.

The invention claimed is:

1. An artificial vascular graft (1) comprising a primary scaffold structure (2) encompassing an inner space (8) of the artificial vascular graft (1), said primary scaffold structure (2) having
   a. an inner surface (21) facing towards said inner space (8) and
   b. an outer surface (20) facing away from said inner space (8) and
   c. a coating (3) on said inner surface (21) and on said outer surface (20) characterized in that
      a plurality of grooves (4) is comprised in said coating (3) of said inner surface (21);
      wherein said primary scaffold structure (2) comprises holes or a mesh structure so that progenitor cells can migrate through an outer surface of said coating (3), said primary scaffold structure (2) and said inner surface of said coating (3) to said inner space (8), and wherein the coating (3) is a cellulose coating comprising a three-dimensional structure pattern of interconnected fibers.

2. The artificial vascular graft according to claim 1, wherein the primary scaffold structure (2) and/or the coating (3) is characterized by a tubular shape.

3. The artificial vascular graft according to claim 2, characterized in that the primary scaffold structure (2) has an outer diameter (X) in the range of about 1.5 mm to 40 mm, and the coating (3) has an inner diameter (Y) in the range of about 1 mm to 35 mm.

4. The artificial vascular graft according to claim 1, characterized in that
the primary scaffold structure (2) and/or the the coating (3) is characterized by a compliance in the range of 400 to 1000%/ 2.93 kPa.

5. The artificial vascular graft according to claim 1, characterized in that
the primary scaffold structure (2) and/or the coating (3) is able to recoil to an original state after a symmetrical, radial expansion perpendicular to thae longitudinal axis of the artificial vascular graft (1), wherein said radial expansion is in the range of 5% to 40% with respect to an original outer diameter (X) of the primary scaffold structure (2) or an original inner diameter (Y) of the coating (3).

6. The artificial vascular graft according to claim 1, characterized in that
the primary scaffold structure (2) comprises a metal or metal alloy.

7. The artificial vascular graft according to claim 1, characterized in that
the primary scaffold structure (2) comprises a shape memory alloy.

8. The artificial vascular graft according to claim 1, characterized in that
the three-dimensional structure pattern comprisesin the form of pores with a diameter of 50 nm to 500 nm.

9. The artificial vascular graft according to claim 1, characterized in that
the coating (3) comprises an inner coating surface (31), which is facing towards the inner space (8) of the artificial vascular graft (1) and a second coating (7) on said inner coating surface (31).

10. The artificial vascular graft according to claim 1, characterized in that
essentially each groove of the plurality of grooves (4) has a width (W) of 0.5 μm to 200 μm.

11. The artificial vascular graft according to claim 1, characterized in that
the coating (3) comprises an inner coating surface (31), which is facing towards the inner space (8) of the artificial vascular graft (1) and a second coating (7) comprising Collagen IV on said inner coating surface (31).

12. The artificial vascular graft according to claim 1, characterized in that
essentially each groove of the plurality of grooves (4) has a width (W) of 1 μm to 50 μm.

13. The artificial vascular graft according to claim 1, characterized in that
essentially each groove of the plurality of grooves (4) has a width (W) of 2 μm to 5 μm.

14. The artificial vascular graft according to claim 1, characterized in that
the primary scaffold structure (2) has an outer diameter (X) in the range of about 1.5 mm to 15 mm and the coating (3) has an inner diameter (Y) in the range of about 3.5 mm to 5 mm.

15. The artificial vascular graft according to claim 1, characterized in that
the primary scaffold structure (2) and/or the coating (3) is characterized by a compliance in the range of 600 to 800%/ 2.93 kPa.

16. The artificial vascular graft according to claim 1, characterized in that
the primary scaffold structure (2) and/or the coating (3) is able to recoil to an original state after a symmetrical, radial expansion perpendicular to the longitudinal axis of the artificial vascular graft (1), wherein said radial expansion is in the range of 15% to 20% with respect to an original outer diameter (X) of the primary scaffold structure (2) or an original inner diameter (Y) of the coating (3).

17. The artificial vascular graft according to claim 1, wherein the coating (3) consists of cellulose in the three-dimensional structure pattern of interconnected fibers.

* * * * *

UNITED STATES PATENT AND TRADEMARK OFFICE
CERTIFICATE OF CORRECTION

PATENT NO. : 11,648,103 B2
APPLICATION NO. : 16/215690
DATED : May 16, 2023
INVENTOR(S) : Bernhard Winkler et al.

It is certified that error appears in the above-identified patent and that said Letters Patent is hereby corrected as shown below:

In the Claims

Claim 8, Column 31, on Lines 41-42: Please replace the phrase "comprisesin the form of pores" with "comprises pores"

Signed and Sealed this
Nineteenth Day of March, 2024

Katherine Kelly Vidal
*Director of the United States Patent and Trademark Office*